(12) United States Patent
Ichiguchi et al.

(10) Patent No.: US 7,449,602 B2
(45) Date of Patent: Nov. 11, 2008

(54) STILBENE DERIVATIVE COMPOUND, PROCESS FOR PRODUCING THE SAME, AND ELECTROPHOTOGRAPHIC PHOTOCONDUCTOR

(75) Inventors: Tetsuya Ichiguchi, Osaka (JP); Yoshio Inagaki, Osaka (JP)

(73) Assignee: Kyocera Mita Corporation, Osaka (JP)

( * ) Notice: Subject to any disclaimer, the term of this patent is extended or adjusted under 35 U.S.C. 154(b) by 715 days.

(21) Appl. No.: 10/943,719

(22) Filed: Sep. 17, 2004

(65) Prior Publication Data
US 2005/0069792 A1 Mar. 31, 2005

(30) Foreign Application Priority Data
Sep. 30, 2003 (JP) ............................. 2003-342021

(51) Int. Cl.
*C07C 211/55* (2006.01)
(52) U.S. Cl. ...................................................... 564/315
(58) Field of Classification Search .................. 564/315
See application file for complete search history.

(56) References Cited
U.S. PATENT DOCUMENTS

| 6,022,998 | A | 2/2000 | Kawaguchi et al. |
| 6,177,220 | B1 | 1/2001 | Watanabe et al. |
| 7,175,954 | B2 * | 2/2007 | Sakimura et al. ......... 430/58.05 |

FOREIGN PATENT DOCUMENTS

| EP | 0 650 956 A1 | 5/1995 |
| JP | 03-149560 | 6/1991 |
| JP | 2000-066419 | 3/2000 |

* cited by examiner

*Primary Examiner*—Peter G O'Sullivan
(74) *Attorney, Agent, or Firm*—Carmody & Torrance LLP

(57) ABSTRACT

A stilbene derivative compound having a specific substituent at the specific position thereof to exert good compatibility with a binder resin and to tend to be uniformly dispersed in a photoconductive layer so as to allow prolonged specified sensitive property, a process for the production thereof, and an electrophotographic photoconductor containing the stilbene derivative compound are provided.

For preparing a stilbene derivative compound represented by the general formula (1), a specified formylated triphenylamine derivative compound and a specified diphosphate ester derivative compound are allowed to be reacted with each other in the presence of a catalyst.

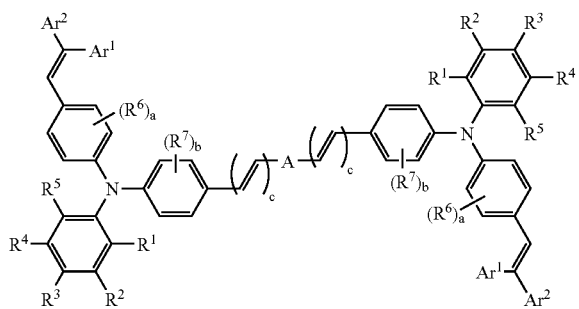

(1)

(wherein "A" is a divalent organic group having aromatic hydrocarbon as a basic skeleton, each of the plural $R^1$ to $R^7$ is a hydrogen atom, a substituted or unsubstituted alkyl group having 1 to 20 carbon atoms, a substituted or unsubstituted aryl group having 6 to 30 carbon atoms, or the like, each of the plural $Ar^1$ and $Ar^2$ is a substituted or unsubstituted aryl group having 6 to 30 carbon atoms, each of repeating numbers a and b is an integer of 0 to 4, and c is an integer of 1 to 3.)

9 Claims, 12 Drawing Sheets

STILBENE DERIVATIVE COMPOUND, PROCESS FOR PRODUCING THE SAME, AND ELECTROPHOTOGRAPHIC PHOTOCONDUCTOR

TECHNICAL FIELD

This invention relates to a stilbene derivative compound having excellent property of photosensitivity for long time, the process for producing the same, and an electrophotographic photoconductor containing such a stilbene derivative compound.

BACKGROUND ART

Conventionally, as electrophotographic photoconductors for image-forming apparatuses and so on, organic photoconductors comprised of organic photoconductive materials such as charge transporting agents, chare generating agents, and binder resins. The organic photoconductor has the advantage of high flexibility in structural design because it can be easily manufactured and an appropriate photoconductive material can be selected from a variety of options, compared with the conventional inorganic photoconductors.

Among the organic photoconductive materials, for example, JP 2000-66419 A discloses a stilbene derivative compound as a charge transporting agent having high charge mobility, which is represented by the following general formula (74);

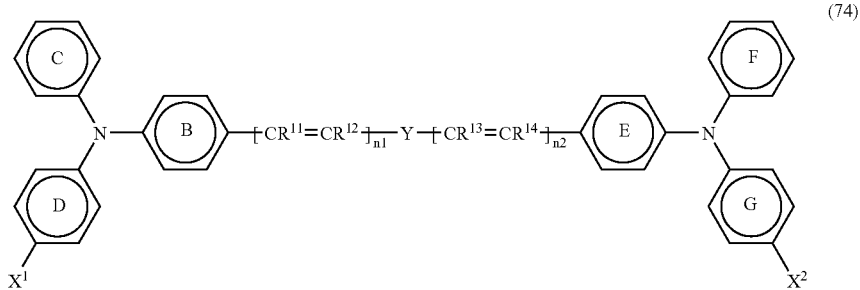
(74)

(wherein, B, C, D, E, F, and G respectively stand for benzene rings which may have substituents, among which at least one may have an alky group or the like; Y stands for a divalent aromatic hydrocarbon residue or the like which may have a substituent; $R^{11}$, $R^{12}$, $R^{13}$, and $R^{14}$ respectively stand for alkyl groups, aryl groups, or the like, which may have substituents; n1 and n2 respectively stand for integers of 1 to 4; and $X^1$ and $X^2$ respectively stand for groups represented by the following general formulas (75) and (76);

(75)

(76)

(wherein $R^{15}$, $R^{16}$, $R^{17}$, $R^{18}$, $R^{19}$, and $R^{20}$ respectively stand for alkyl groups, aryl groups, or the like, which may have substituents.)

In addition, JP 03-149560 A discloses a stilbene derivative compound as a charge transporting agent having high charge mobility, which is represented by the general formula (77);

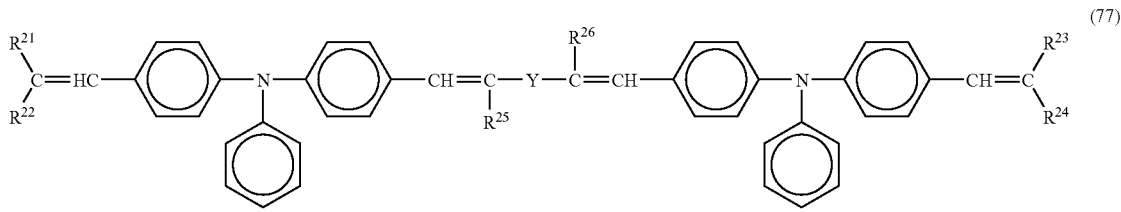
(77)

(wherein Y stands for an organic group such as a substituted or unsubstituted phenylene group, or an organic group represented by the formula (78) described below, and $R^{21}$ to $R^{26}$ respectively stand for substituted or unsubstituted aryl groups, alkyl groups, or the like)

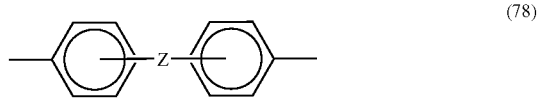
(78)

(wherein Z stands for an oxygen atom, a sulfur atom, or the like, or an organic group represented by the following formula (79));

(79)

(wherein $R^{27}$ and $R^{28}$ respectively stand for alkyl groups, aryl groups, or the like.)

Here, the stilbene derivative compound disclosed in JP 2000-66419 A is defied as one having at least one alkyl group in the benzene rings B-G of the general formula (74). However, the stilbene derivative compound described in a concrete example has a central structure with a divalent phenyl group having a coupling hand at the para position, a divalent diphenyl group having coupling hands at the respective prara positions, or a divalent thiophene group in which a substituent on the benzene ring C is positioned at a meta position or a para position. Therefore, the concrete example of the stilbene derivative compound disclosed in JP 2000-66419 A shows poor compatibility with a binder resin and is difficult to uniformly disperse in a photoconductive layer. Therefore, there has been found a disadvantage in that the prolonged use of such a compound tends to cause crystallization. In other words, the disclosed stilbene derivative compound has a problem of insufficient charge mobility when it has been used as a charge transporting agent in a photoconductor for long periods of time in spite of showing high charge mobility in the initial stages.

Furthermore, in JP 2000-66419 A, there is another problem in that the desired stilbene derivative compound cannot be obtained in a stable manner because of low production efficiency in the process for producing a stilbene derivative compound.

Moreover, the stilbene derivative compound disclosed in JP 03-149560 A showed a problem of poor compatibility with a binder resin because of no substituent in the benzene ring in the form of a triphenylamine structure on the end of the molecule. Therefore, there is a problem in that the compound is not only hardly dispersed in the photosensitive layer uniformly but also subjected to be crystallized when it is used for long periods of time.

As a consequence, for solving the problems involved in the conventional stilbene derivative compounds and for providing a suitable compound as a hole transporting agent or the like of an electrophotographic photoconductor, the present invention intends to provide:

1) a specific stilbene derivative compound, which is capable of improving its photosensitive property for long periods of time;

2) a specific stilbene derivative compound, which is capable of effectively preventing the crystallization thereof for long periods of time;

3) a process for stable production of the specific stilbene derivative compound; and 4) an electrophotographic photoconductor having excellent photosensitive property for long periods of time, which is attained by containing the specific stilbene derivative compound.

DISCLOSURE OF THE INVENTION

[1] According to the invention, the stilbene derivative compound represented by the following general formula (1) is provided, thereby solving the problems described above;

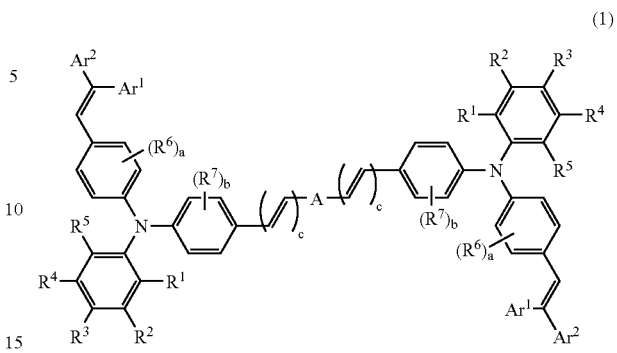

(1)

(wherein "A" is a divalent organic group having an aromatic hydrocarbon as a basic skeleton; plural $R^1$ to $R^7$ are independent substituents, respectively, each of which is a hydrogen atom, a halogen atom, a substituted or unsubstituted alkyl group having 1 to 20 carbon atoms, a substituted or unsubstituted halogenated alkyl group having 1 to 20 carbon atoms, a substituted or unsubstituted alkoxy group having 1 to 20 carbon atoms, a substituted or unsubstituted aryl group having 6 to 30 carbon atoms, or a substituted or unsubstituted amino group, or two of the plural $R^1$ to $R^7$ may be bound or condensed to form a carbon ring structure; plural $Ar^1$ and $Ar^2$ are independent from each other, each of which is a substituted or unsubstituted aryl group having 6 to 30 carbon atoms; a and b are numbers of repetition, each of which is an integer from 0 to 4; and c is an integer from 1 to 3, but at least one of the plural $R^1$ and $R^5$ is a substituent other than a hydrogen atom when A is a divalent organic group represented by the formula (2), while at least one of the plural $R^1$ to $R^7$ is a substituent other than a hydrogen atom when A is one other than the divalent organic group represented by the formula (2));

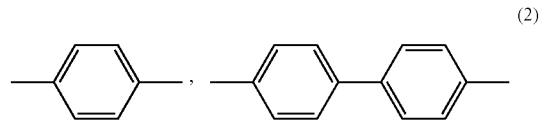

(2)

In other words, the stilbene derivative compound represented by the general formula (1) has a specific substituent at the specific position thereof to cause specified steric hindrance. Hence, the compound can be characterized in that it shows good compatibility with a binder resin and tends to be uniformly dispersed in a photosensitive layer. Therefore, the stilbene derivative compound is hardly crystallized when it is used as a hole transporting agent or the like of an electrophotographic photoconductor and thus an electrophotographic photoconductor capable of keeping specified photosensitivity for long periods of time can be obtained. Here, the aromatic hydrocarbon represented by A in the general formula (1) is a cyclic compound comprising carbon and hydrogen atoms with a benzene ring as a basic skeleton, such as benzene, toluene, naphthalene, and anthracene.

[2] In addition, an another aspect of the present invention, as represented by the reaction formula (1), is a process for the production of a stilbene derivative compound represented by the general formula (1), characterized by reacting a formylated triphenylamine derivative compound represented by the general formula (4) with a diphosphate ester derivative compound represented by the general formula (5) in the presence of a catalyst.

Therefore, by producing in this way, the stilbene derivative compound having a specific substituent at the specific position thereof can be stably obtained. In consequence, a specified stilbene derivative compound, which shows excellent compatibility with a binder resin and high charge mobility and is capable of effectively preventing crystallization, can be obtained in high yield.

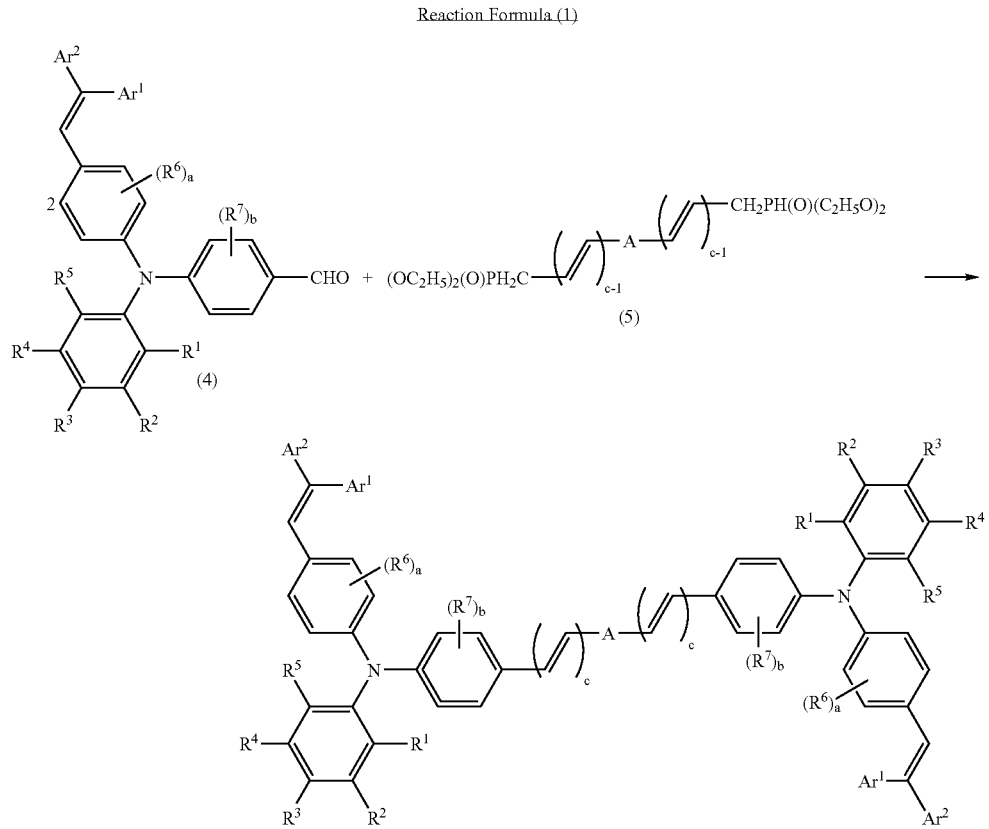

(wherein "A", plural $R^1$ to $R^7$, plural $Ar^1$ and $Ar^2$, repeating numbers a, b, and c are the same as those defined in the general formula (1) respectively.)

[3] A further aspect of the present invention is an electrophotographic photoconductor, in which a photosensitive layer is mounted on an electroconductive substrate, characterized by comprising a stilbene derivative compound represented by the general formula (1) described above.

Therefore, by constructing the electrophotographic photoconductor in this way, it is allowed to obtain the electrophotographic photoconductor comprising a stilbene derivative compound that shows excellent compatibility with a binder resin and high charge mobility and is capable of keeping specified photosensitivity for long periods of time.

Figure 5:
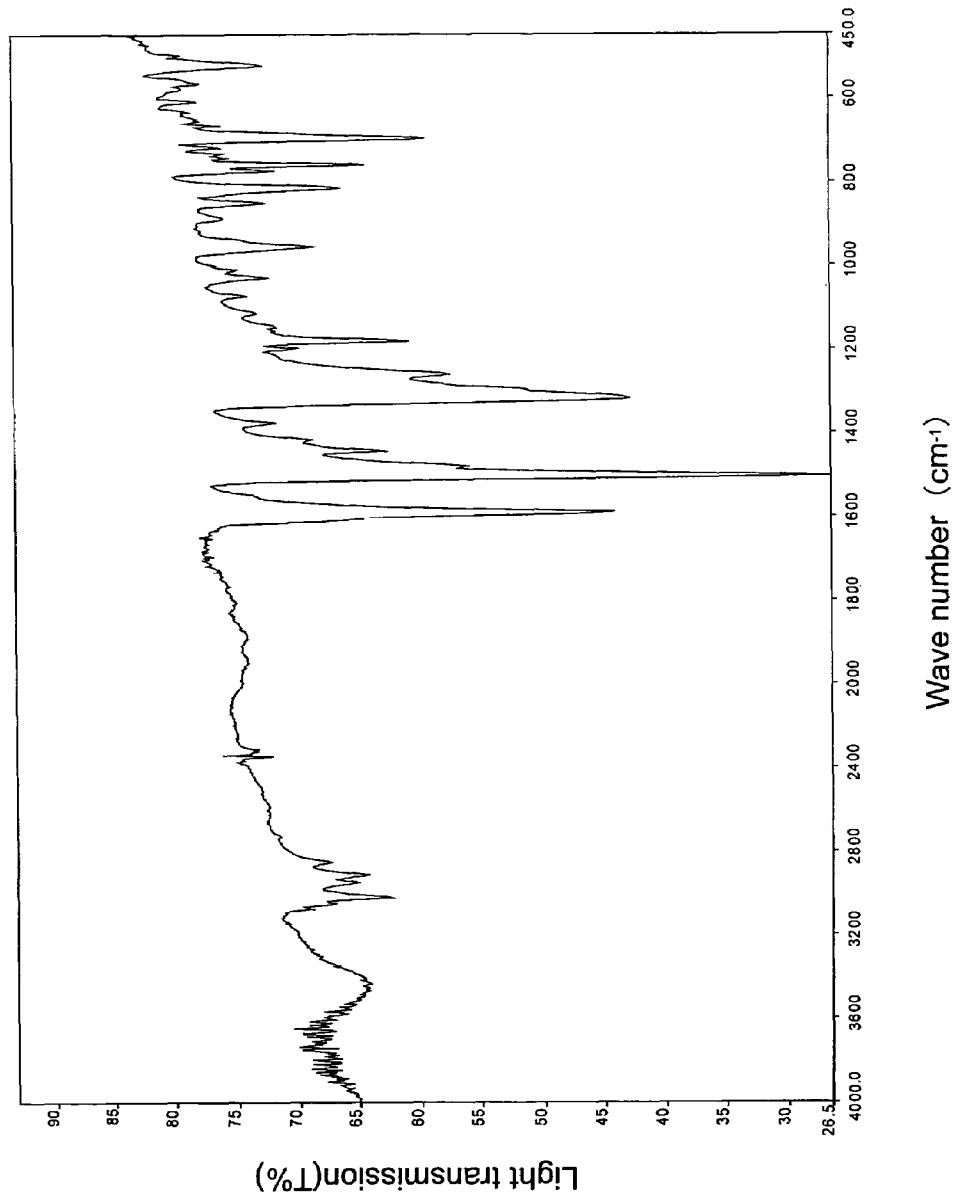

FIG. 5 is a diagram provided for illustrating the infrared spectroscopic (IR) chart of a stilbene derivative compound represented by the formula (25).

Figure 6:
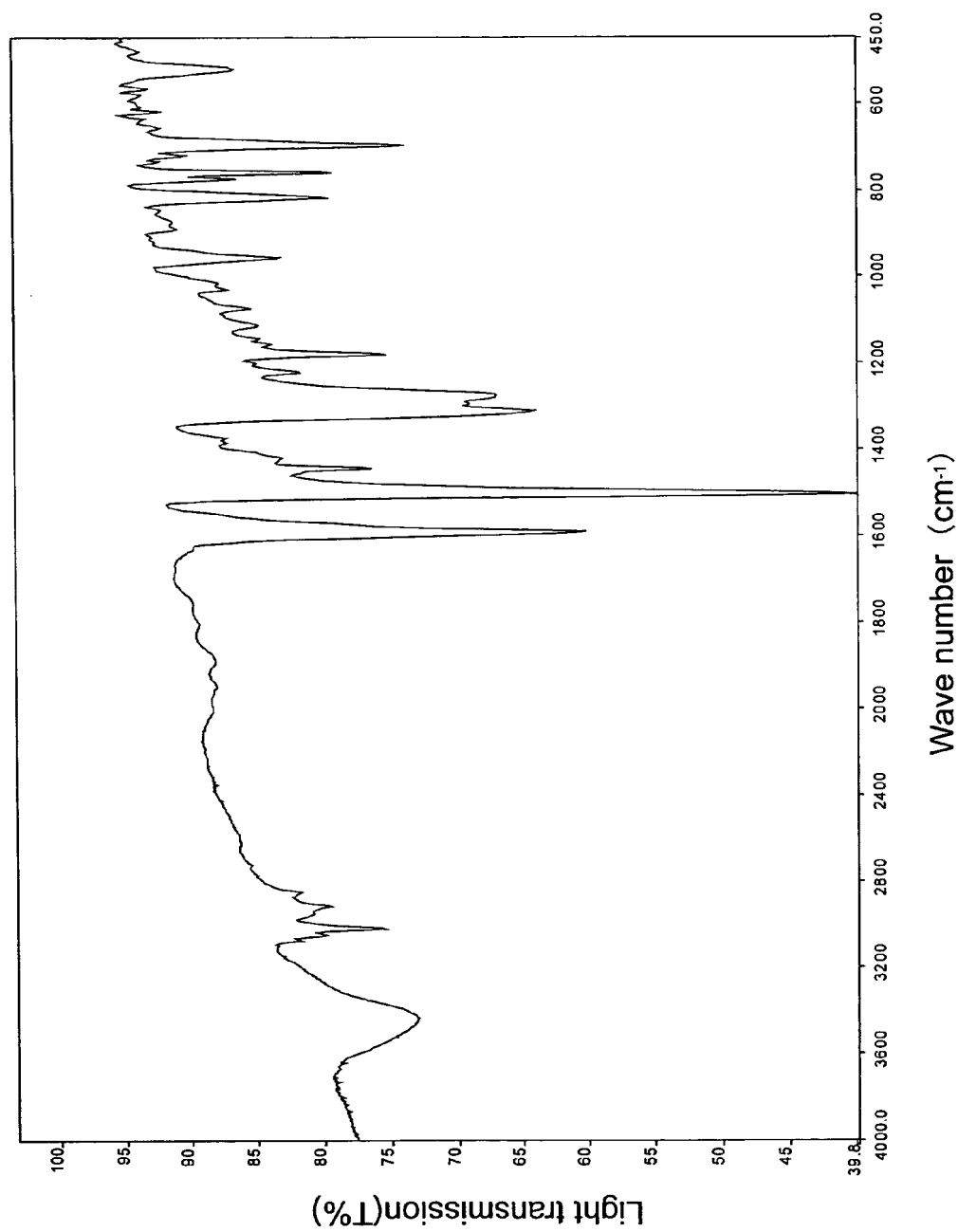

FIG. 6 is a diagram provided for illustrating the infrared spectroscopic (IR) chart of a stilbene derivative compound represented by the formula (29).

Figure 7:
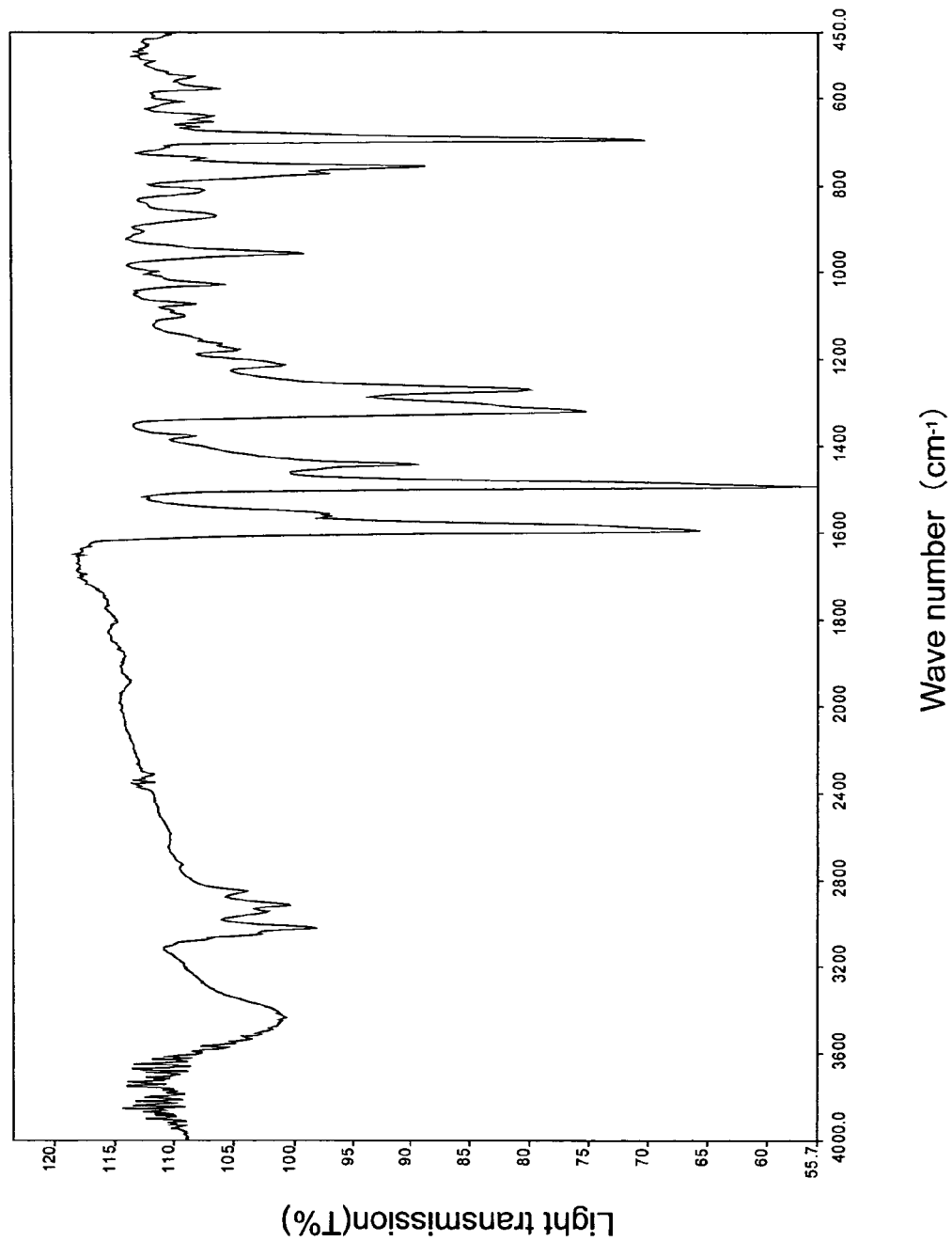

FIG. 7 is a diagram provided for illustrating the infrared spectroscopic (IR) chart of a stilbene derivative compound represented by the formula (30).

Figure 8:
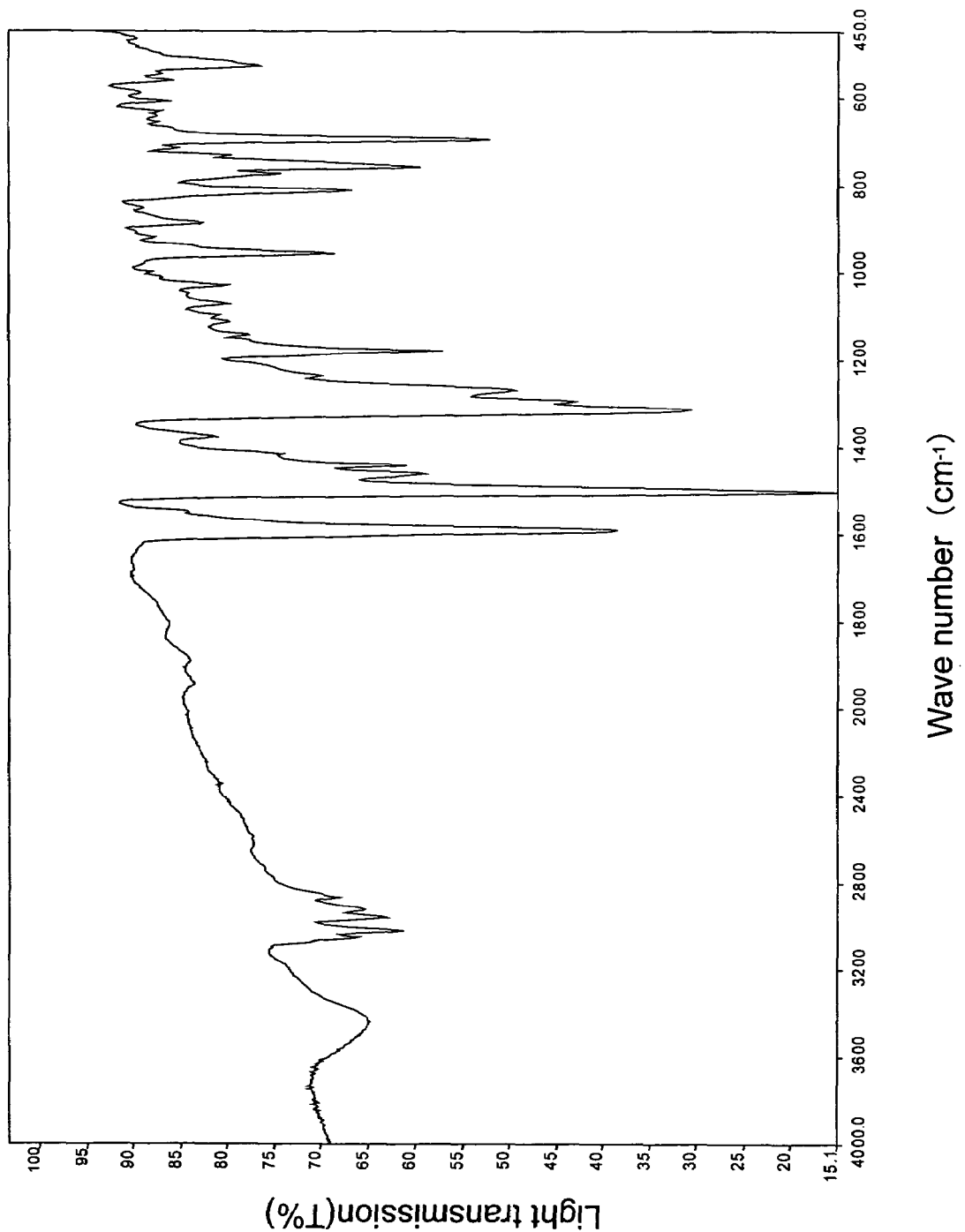

FIG. 8 is a diagram provided for illustrating the infrared spectroscopic (IR) chart of a stilbene derivative compound represented by the formula (33).

Figure 9:
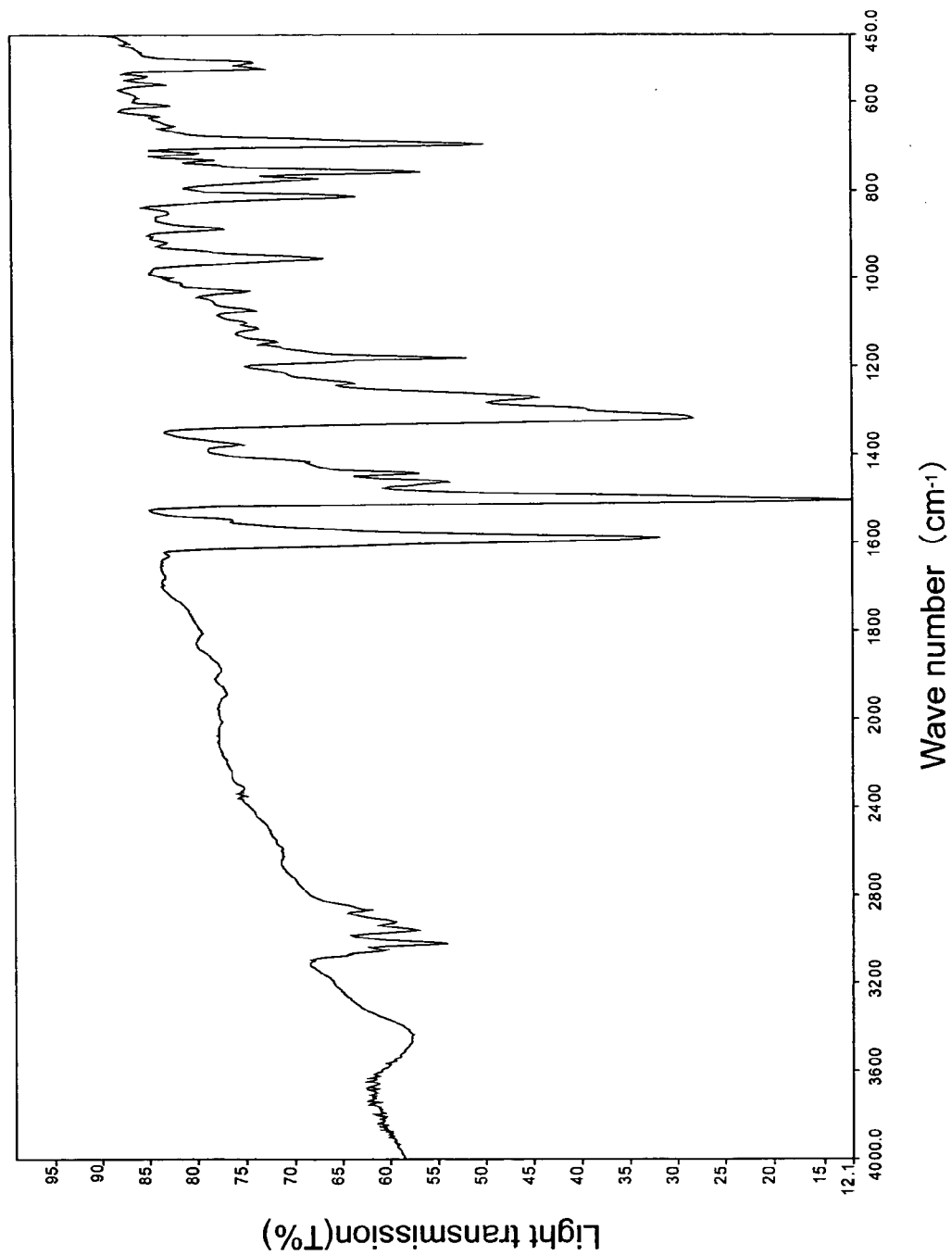

FIG. 9 is a diagram provided for illustrating the infrared spectroscopic (IR) chart of a stilbene derivative compound represented by the formula (34).

Figure 10:
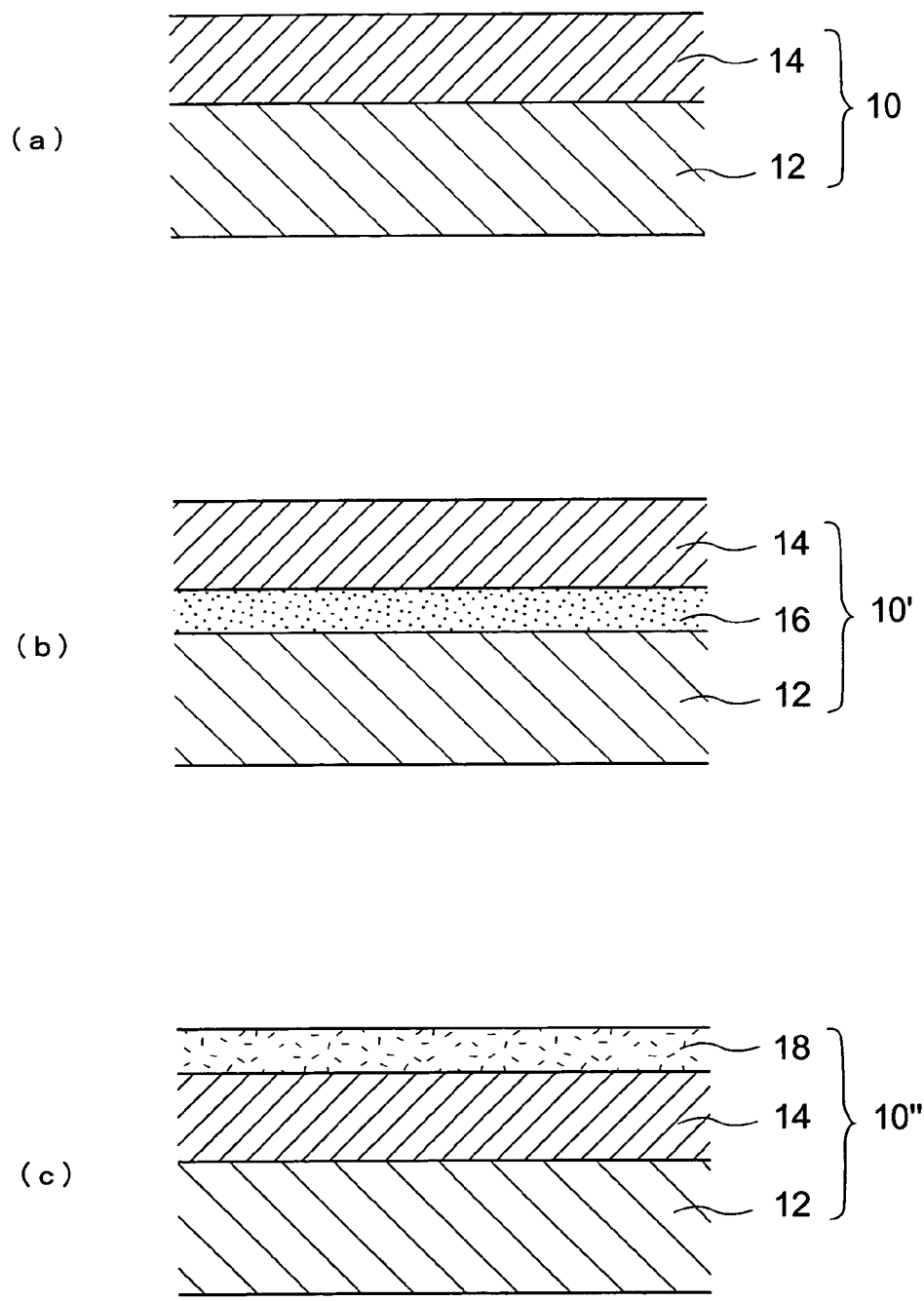

FIG. 10(*a*) to (*c*) are a diagram provided for illustrating basic and modified structures of a monolayer type photoconductor, respectively.

Figure 11:
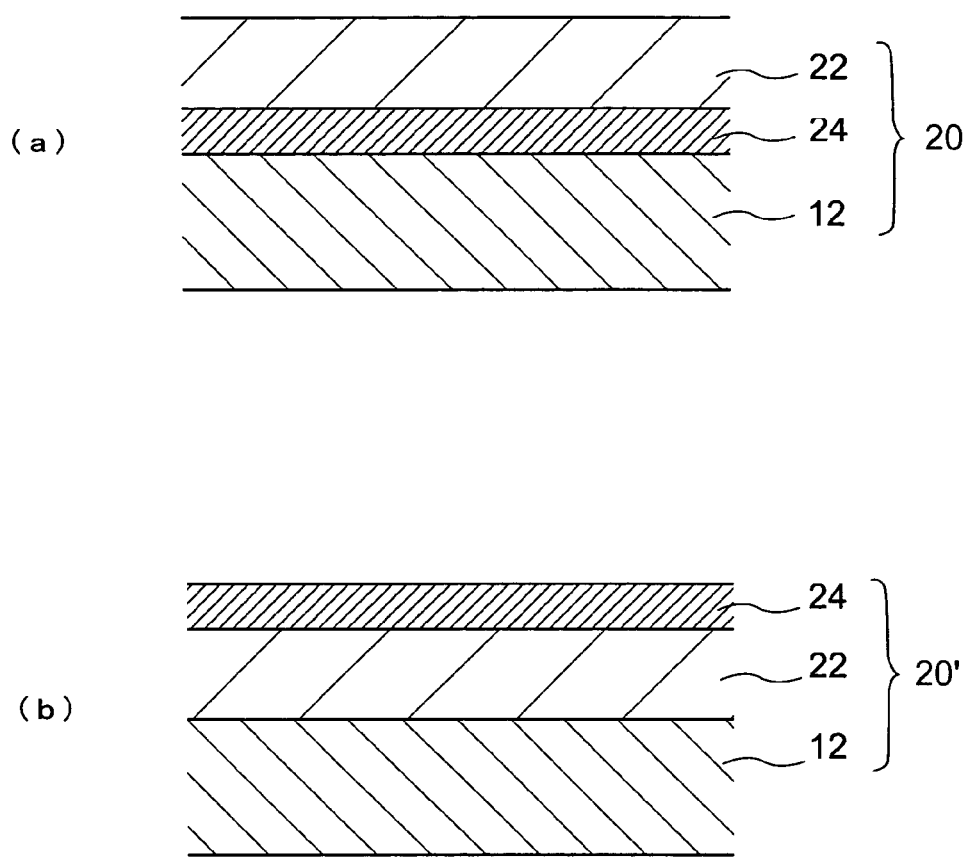

FIG. 11(*a*) and (*b*) are a diagram provided for illustrating basic and modified structures of a monolayer type photoconductor, respectively.

Figure 12:
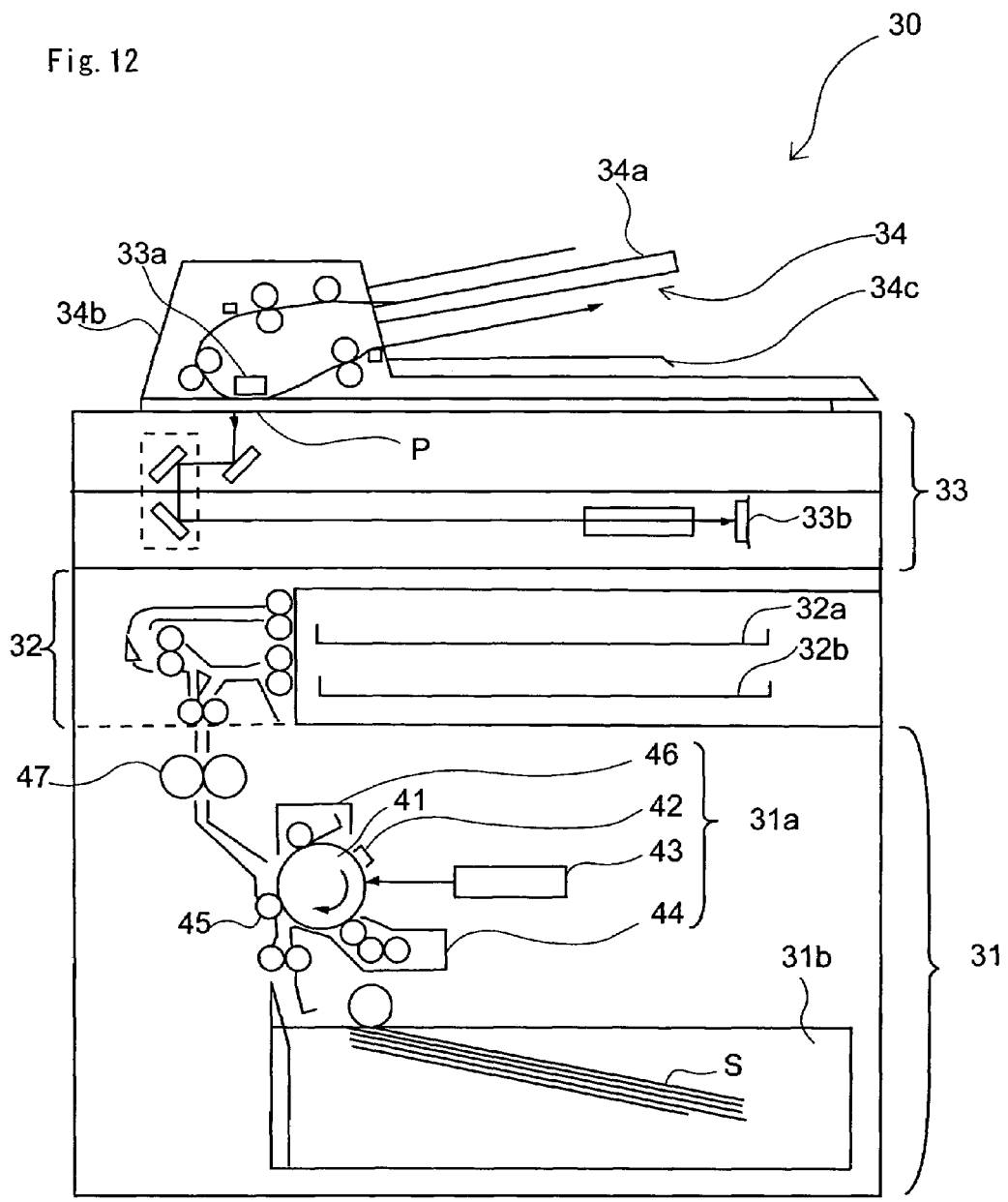

FIG. 12 is a diagram provided for illustrating an image-forming apparatus equipped with an electrophotographic photoconductor.

BEST MODE FOR CARRYING OUT THE INVENTION

[First Embodiment]

A first embodiment is a stilbene derivative compound represented by the general formula (1) described below.

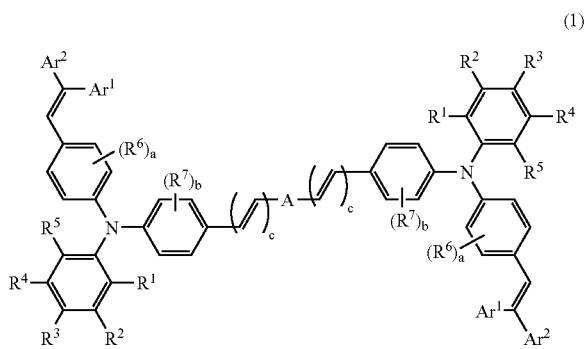

(1)

(wherein "A" is a divalent organic group having an aromatic hydrocarbon as a basic skeleton; plural $R^1$ to $R^7$ are independent substituents, respectively, each of which is a hydrogen atom, a halogen atom, a substituted or unsubstituted alkyl group having 1 to 20 carbon atoms, a substituted or unsubstituted halogenated alkyl group having 1 to 20 carbon atoms, a substituted or unsubstituted alkoxy group having 1 to 20 carbon atoms, a substituted or unsubstituted aryl group having 6 to 30 carbon atoms, or a substituted or unsubstituted amino group, or two of the plural $R^1$ to $R^7$ may be bound or condensed to form a carbon ring structure; plural $Ar^1$ and $Ar^2$ are independent from each other, each of which is a substituted or unsubstituted aryl group having 6 to 30 carbon atoms; a and b are numbers of repetition, each of which is an integer from 0 to 4; and c is an integer from 1 to 3, but at least one of the plural $R^1$ and $R^5$ is a substituent other than a hydrogen atom when A is a divalent organic group represented by the formula (2), while at least one of the plural $R^1$ to $R^7$ is a substituent other than a hydrogen atom when A is one other than the divalent organic group represented by the formula (2));

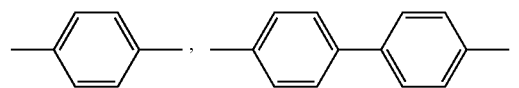

(2)

1. Substituents

In addition, for constructing the stilbene derivative compound of the present invention, each of plural $Ar^1$ and $Ar^2$ in the general formula (1) is preferably a substituted or unsubstituted aryl groups having 6 to 14 carbon atoms. This is because of its characteristic features of extended intramolecular conjugation and excellent charge mobility. Therefore, an electrophotographic photoconductor having excellent photosensitive property can be obtained by the use of such a stilbene derivative compound as a charge transporting agent (hole transporting agent) in an electrophotographic photoconductor.

For constructing the stilbene derivative compound of the present invention, when A in the general formula (1) is a divalent organic group represented by the formula (2), at least one of the plural $R^1$ and $R^5$ is preferably a substituted or unsubstituted alkyl group having 1 to 10 carbon atoms or a substituted or unsubstituted alkoxy group having 1 to 10 carbon atoms. This is because at least one or both of $R^1$ and $R^5$ in the general formula (1) is a specified alkyl group or the like to cause a decrease in planarity of a hole transporting agent due to steric hindrance. Therefore, the compound is excellent in compatibility with a binder resin and can be uniformly dispersed in a photosensitive layer. Thus, it brings about an effect of proving the compound with excellent photosensitive property in addition to effectively prevent the compound from crystallization for long periods of time.

For constructing the stilbene derivative compound of the present invention, when A in the general formula (1) is a divalent organic solvent having an aromatic hydrocarbon as a basic skeleton other than one expressed by the general formula (2), at least one of the plural $R^1$ to $R^7$ is preferably a substituted or unsubstituted alkyl group having 1 to 10 carbon atoms or a substituted or unsubstituted alkoxy group having 1 to 10 carbon atoms. This is because at least one of the $R^1$ to $R^7$ of the general formula (1) is a specified alkyl group or the like and thus the compound can be more excellent in compatibility with a binder resin and can be uniformly dispersed in a photosensitive layer. It brings about an effect of proving the compound with excellent photosensitive property in addition to more effectively prevent the compound from crystallization for long periods of time.

For constructing the stilbene derivative compound of the present invention, it is preferable that two of the plural $R^1$ to $R^5$ in the general formula (1) are respectively of carbocyclic ring structures having 3 to 6 carbon atoms. This is because of extended intramolecular conjugation and a more increase in charge mobility.

Moreover, the concrete examples of the phenyl group having the substituent of the plural $R^1$ to $R^5$ in the general formula (1) include a phenyl group represented by formula (15) described below. In addition, for making the binding status clear, nitrogen atoms are also represented.

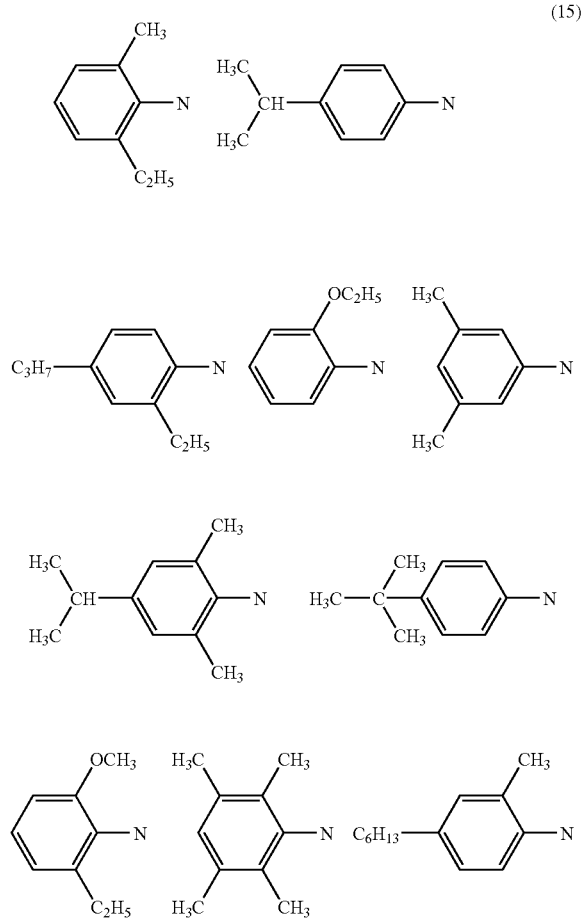
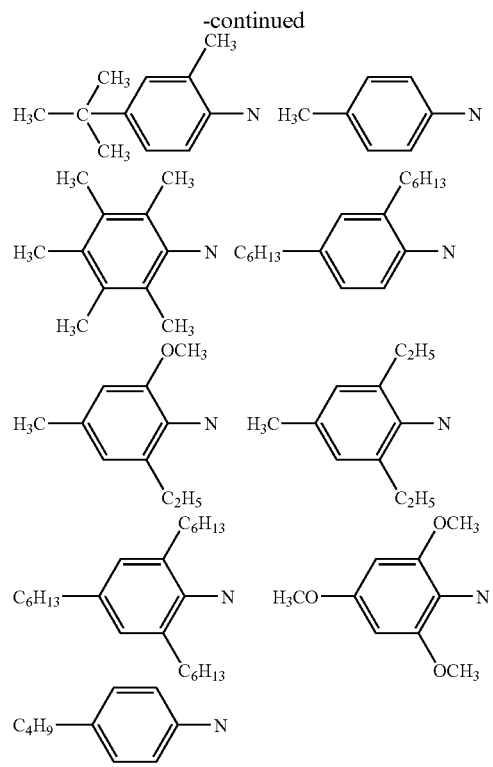
2. Types
For constituting the stilbene derivative compound of the present invention, the stilbene derivative compound represented by the general formula (1) is preferably a stilbene derivative compound represented by the general formula (3) described below.
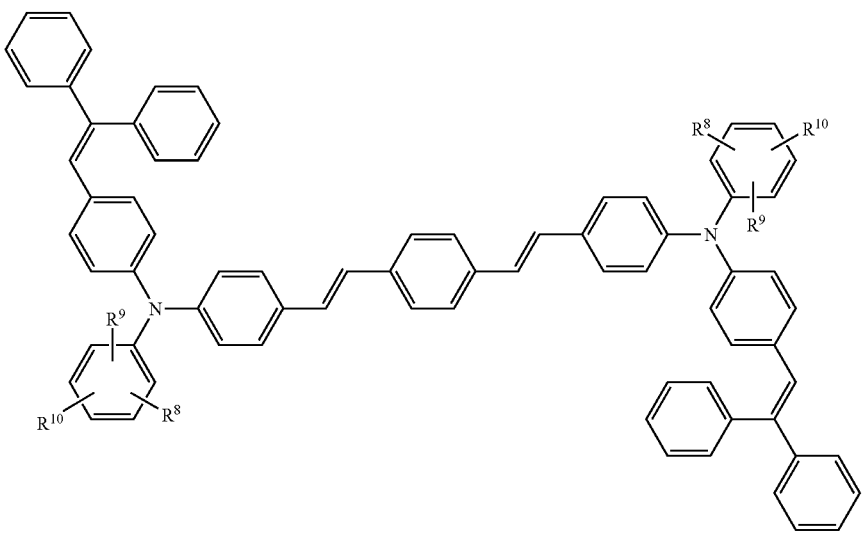

(wherein plural $R^8$ to $R^{10}$ are independent substituents, respectively, each of which is a hydrogen atom, a halogen atom, a substituted or unsubstituted alkyl group having 1 to 20 carbon atoms, a substituted or unsubstituted halogenated alkoxy group having 1 to 20 carbon atoms, a substituted or unsubstituted aryl group having 6 to 20 carbon atoms, or a substituted or unsubstituted amino group, but at least one of the plural $R^8$, $R^9$, and $R^{10}$ is a substituent positioned at an ortho position of the benzene ring other than a hydrogen atom.)

In addition, for constituting the stilbene derivative compound of the present invention, at least one of the plural $R^8$, $R^9$, and $R^{10}$ in the general formula (3) is preferably a substituted or unsubstituted alkyl group having 1 to 6 carbon atoms positioned at an ortho position of the benzene ring coupled with a nitrogen atom. This is because of further excellent compatibility with a binder resin and further excellent solubility in solvent due to the fact that at least one of the plural $R^8$, $R^9$, and $R^{10}$ in the general formula (3) is the specified alkyl group substituted at the specified position thereof. Therefore the compound can be uniformly dispersed in a photosensitive layer and thus it can be effectively prevented from crystallization, thereby obtaining excellent effects in photosensitivity and durability.

Consequently, at least one of the plural $R^8$, $R^9$ and $R^{10}$ in the general formula (3) is preferably a substituted or unsubstituted alkyl group having 2 to 10 carbon atoms.

Moreover, for constituting the stilbene derivative compound of the present invention, two of the plural $R^8$, $R^9$, and $R^{10}$ in the general formula (3) are preferably the specified alkyl groups substituted at the specified positions, respectively. This is because it is further excellent in compatibility with binder resin and solubility in solvent.

3. Concrete Examples

Furthermore, as the concrete examples of the stilbene derivative compounds represented by the general formulas (1) and (3), stilbene derivative compounds (HTM-A to Y) represented by the formulas (16) to (40) described below will be described. For reference to understand their structures, the infrared spectroscopy (IR) charts of the stilbene derivative compounds (HTM-A, J, N, O, R, and S) represented by the formulas (16), (25), (29), (30), and (31) are shown in FIG. 1 and FIGS. 5 to 9, respectively, and the proton-NMR charts (an overall view and two enlarged views) of the stilbene derivative compound represented by the formula (15) are shown in FIGS. 2, 3, and 4, respectively.

(16)

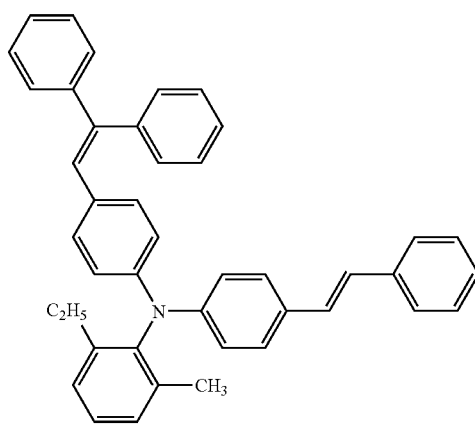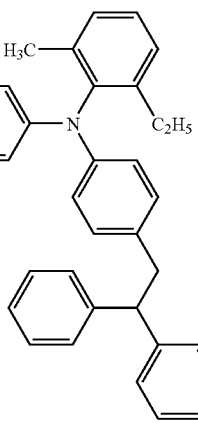

(HTM-A)

(17)

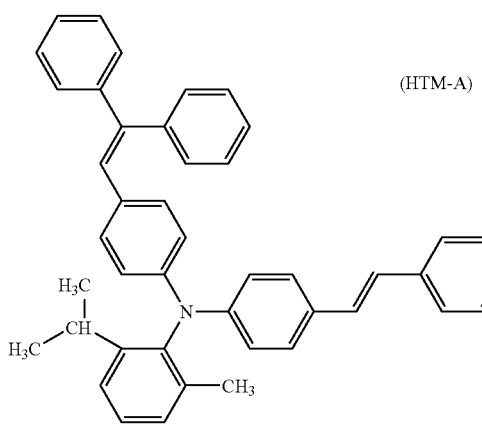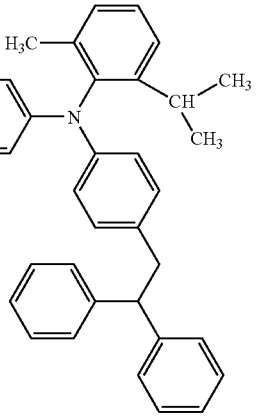

(HTM-B)

-continued
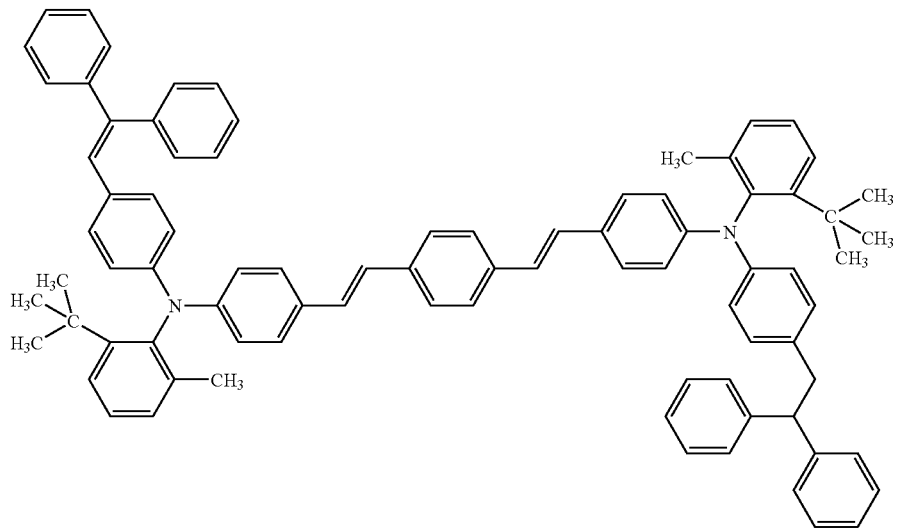
(18)
(HTM-C)
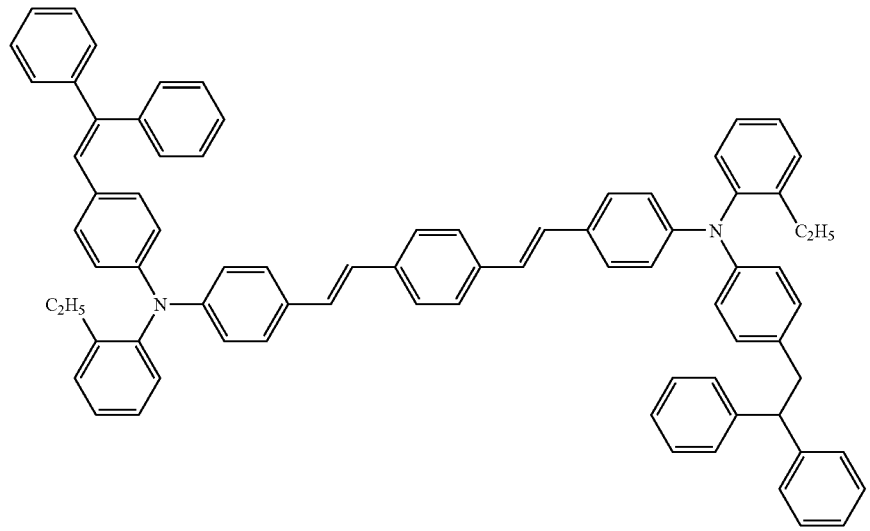
(19)
(HTM-D)

(20)
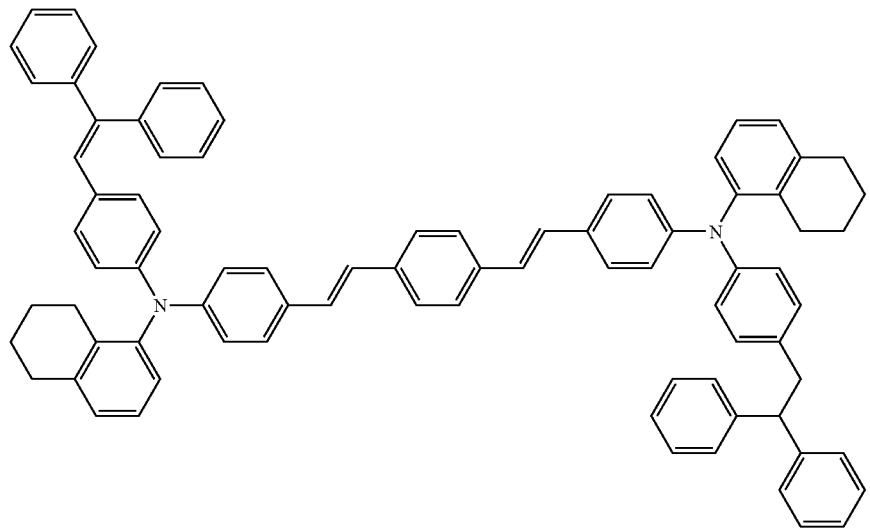
(HTM-E)
(21)
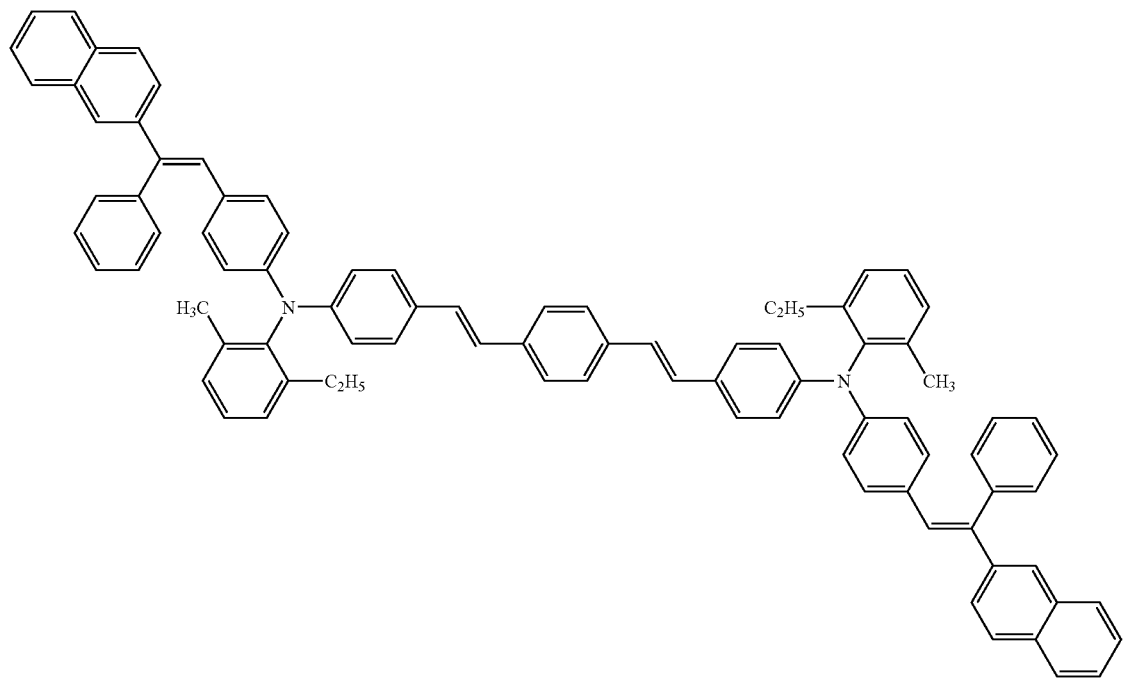
(HTM-F)

(22)
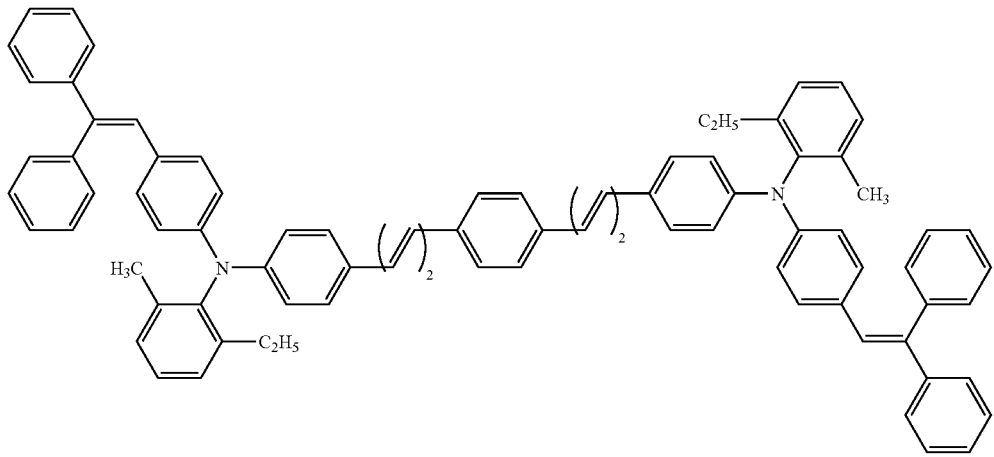
(HTM-G)
(23)
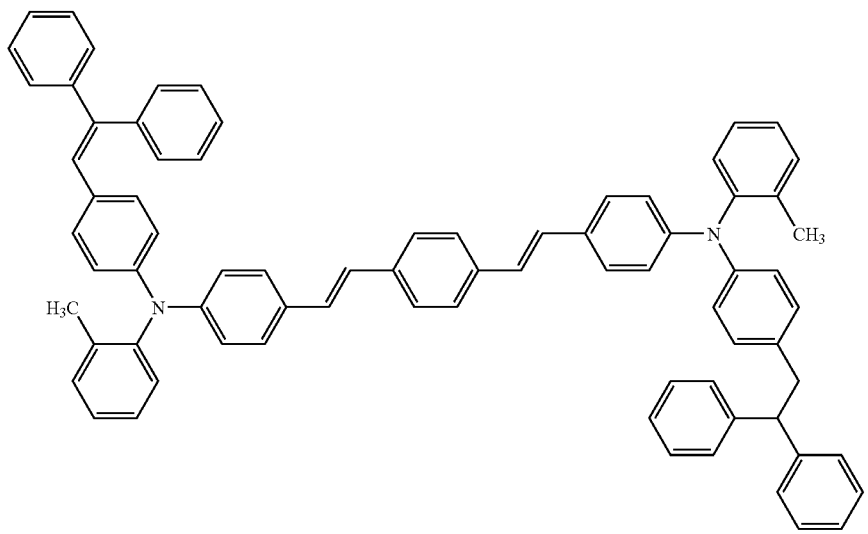
(HTM-H)
(24)
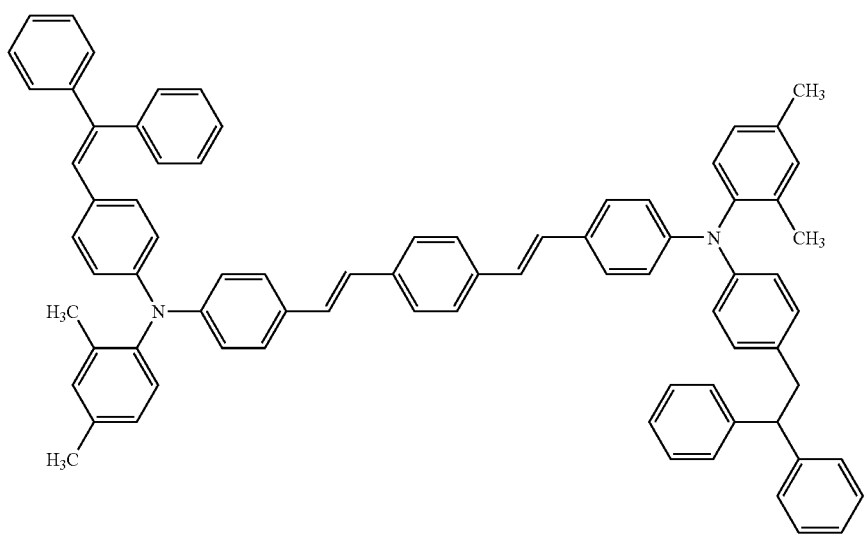
(HTM-I)

-continued
(25)
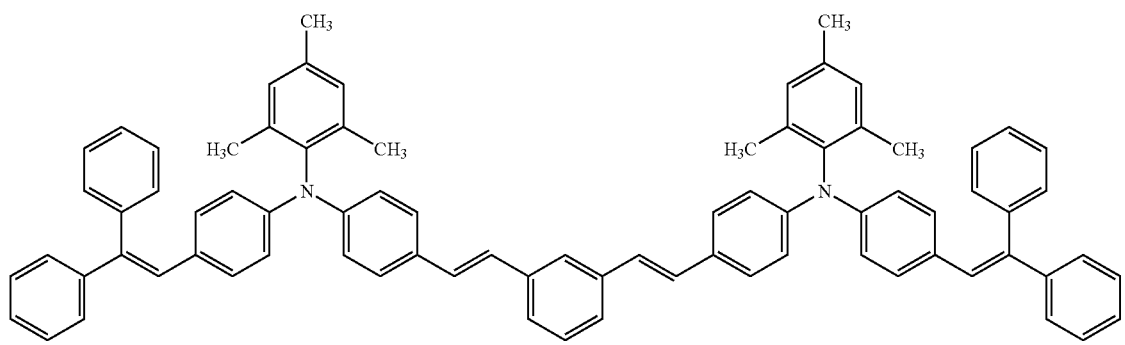
(HTM-J)
(26)
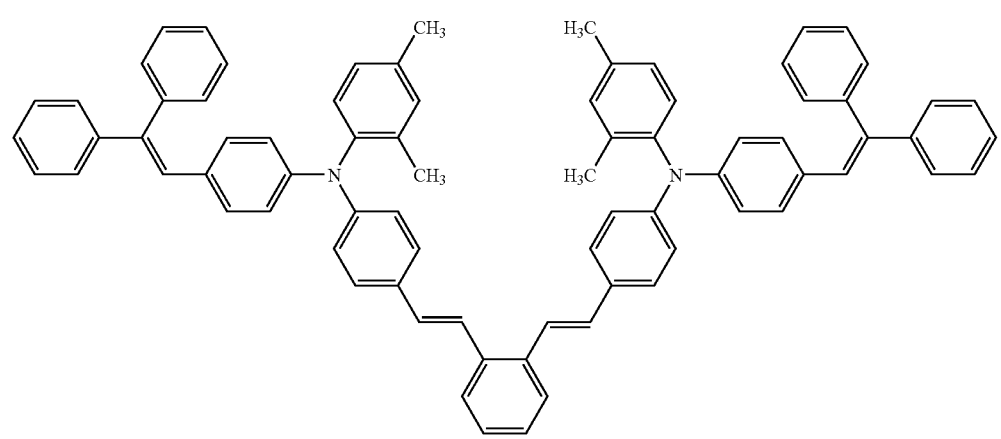
(HTM-K)
(27)
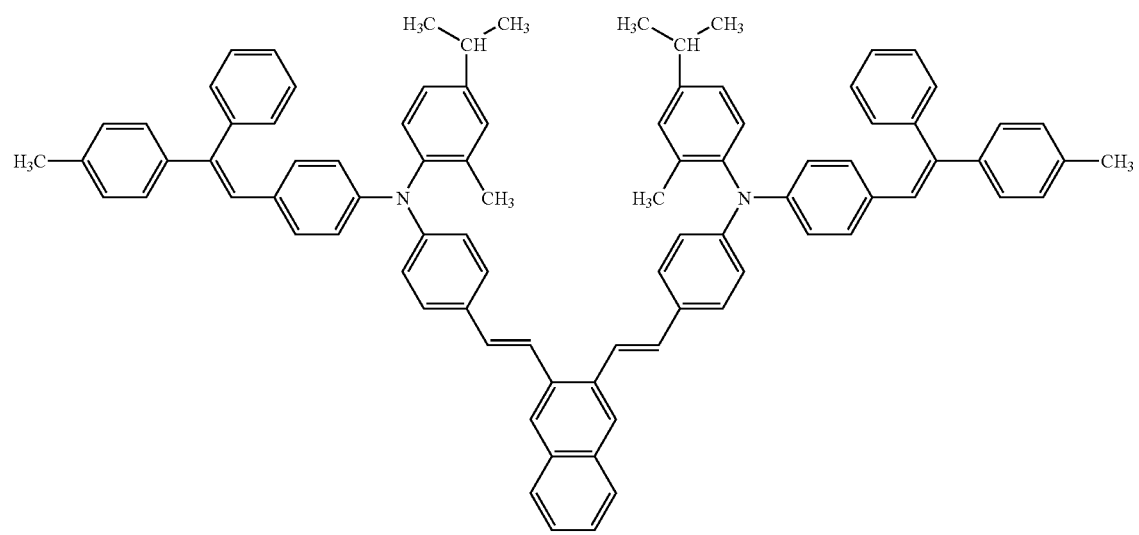
(HTM-L)

(28)
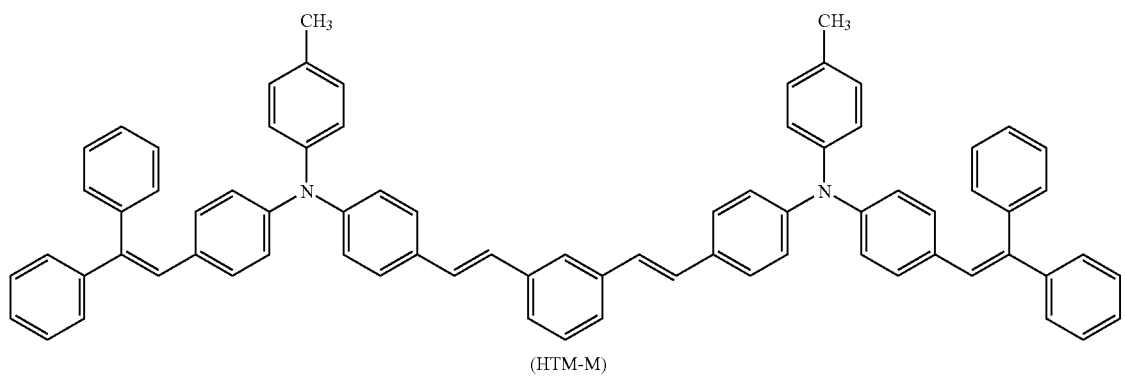
(HTM-M)
(29)
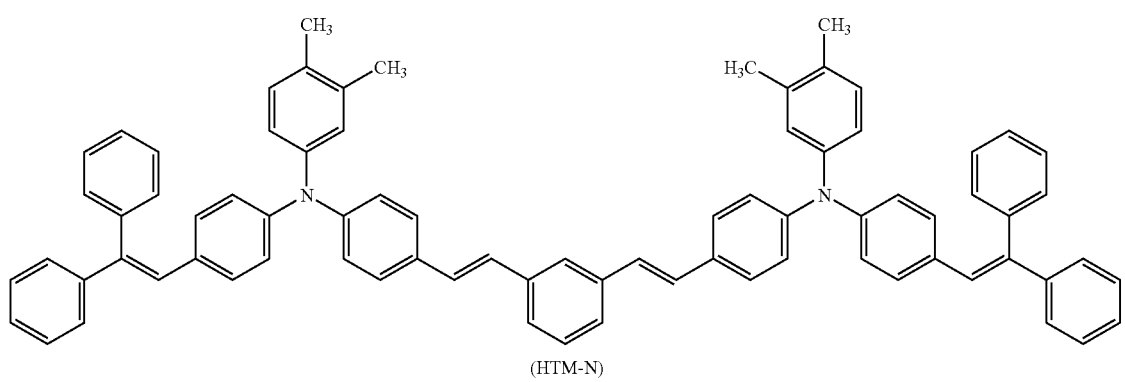
(HTM-N)
(30)
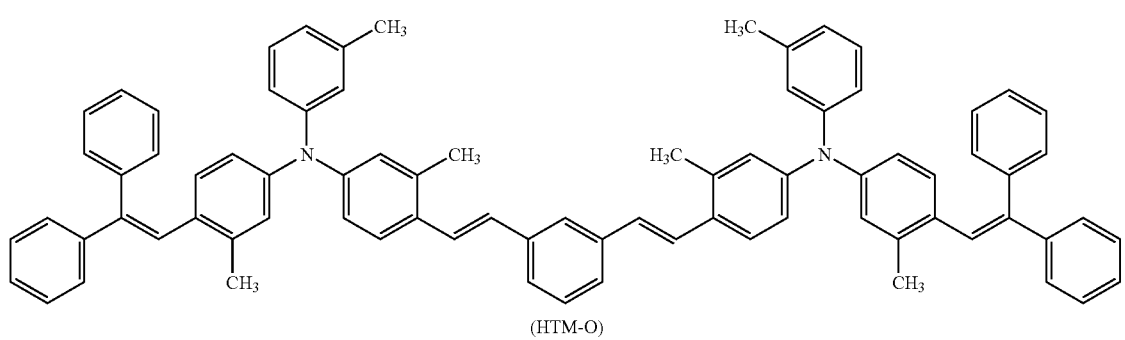
(HTM-O)
(31)
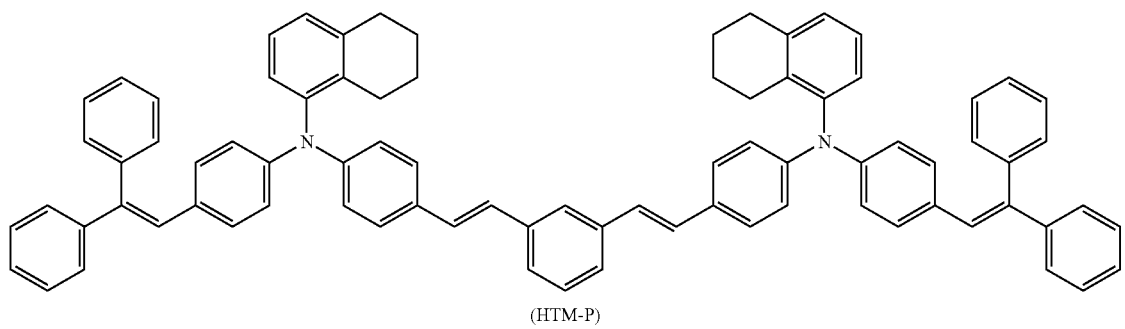
(HTM-P)

-continued
(32)
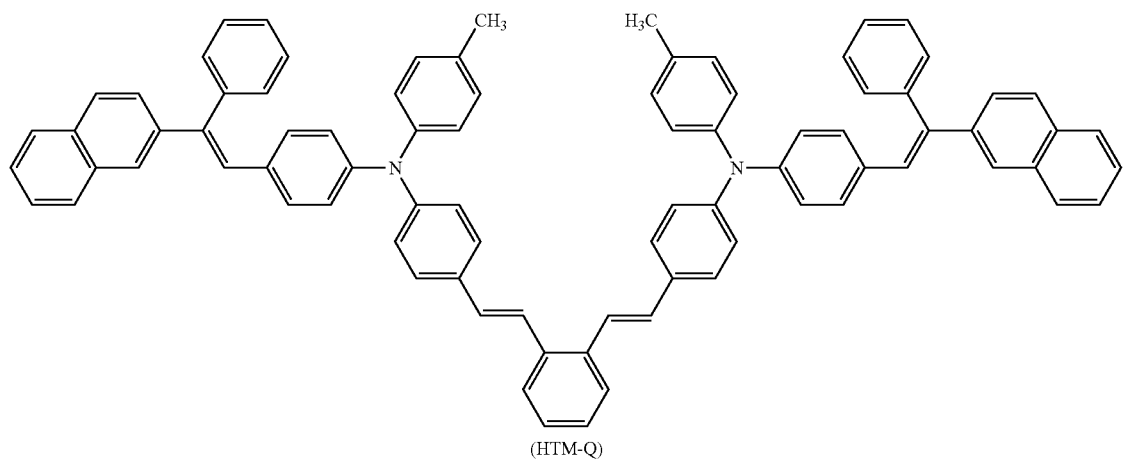
(HTM-Q)
(33)
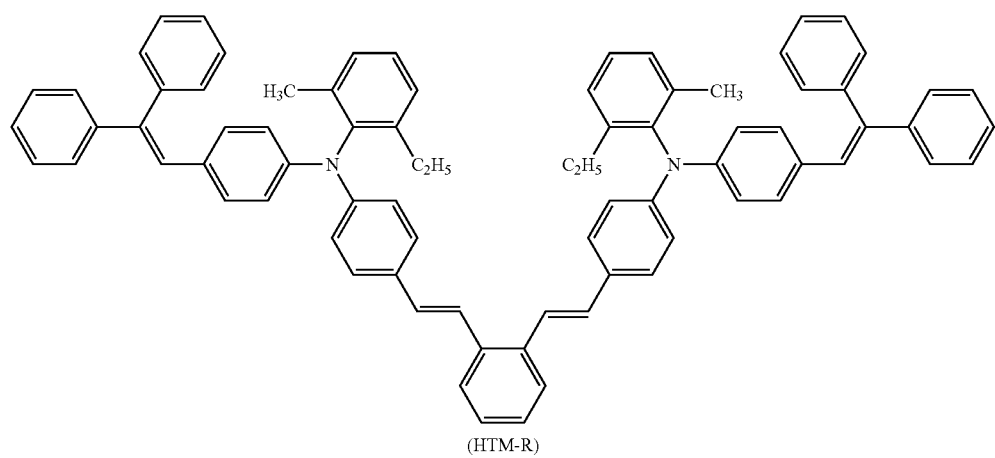
(HTM-R)
(34)
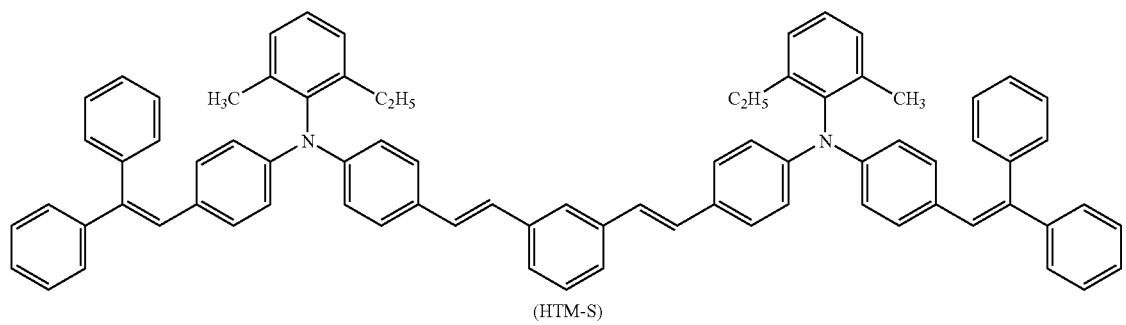
(HTM-S)

(35)
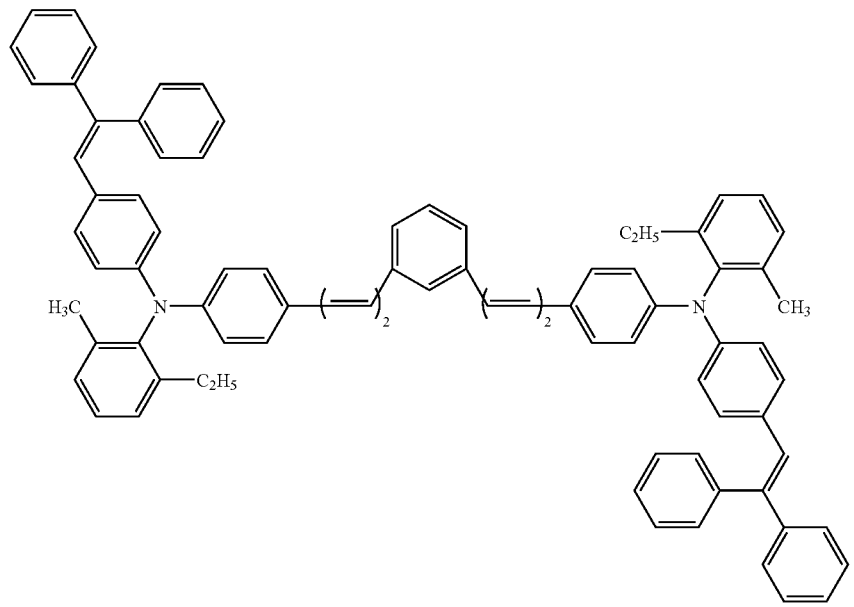
(HTM-T)
(36)
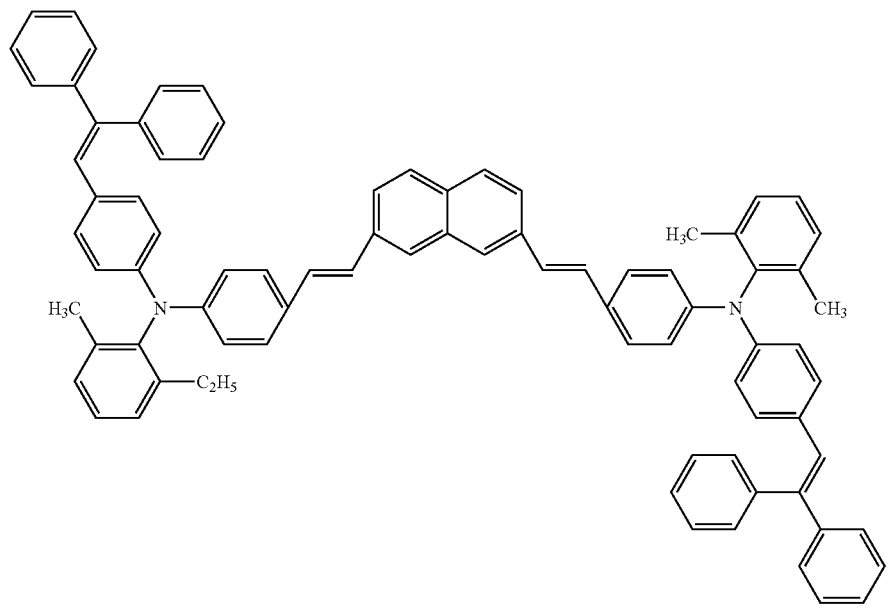
(HTM-U)

(37)
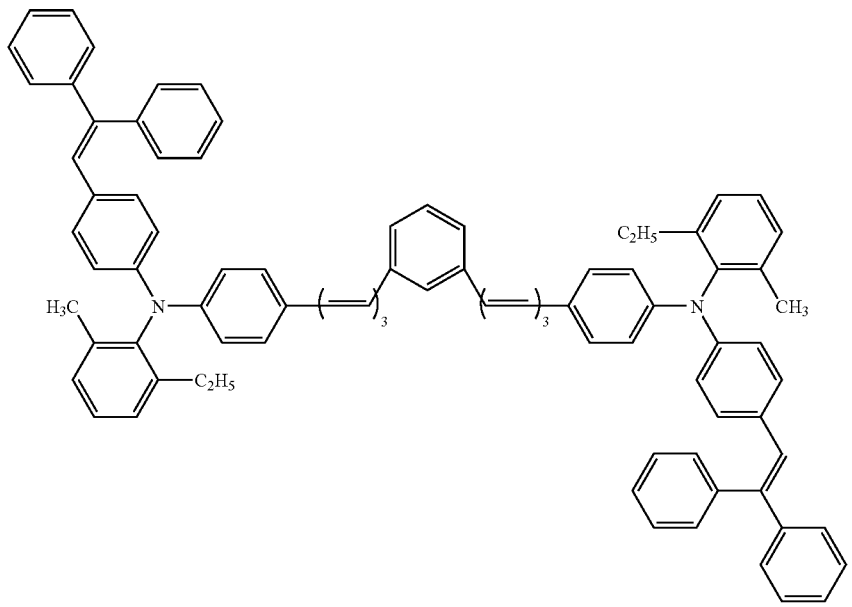
(HTM-V)
(38)
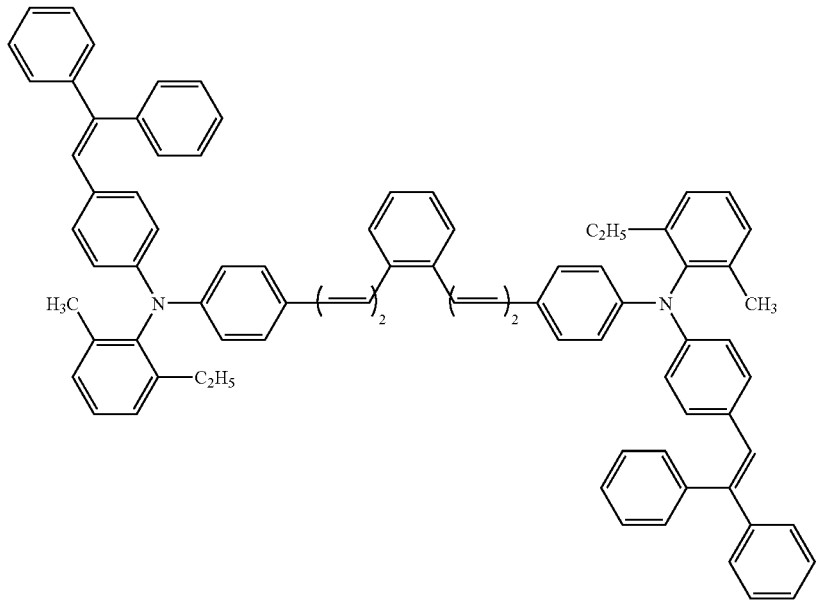
(HTM-W)

-continued

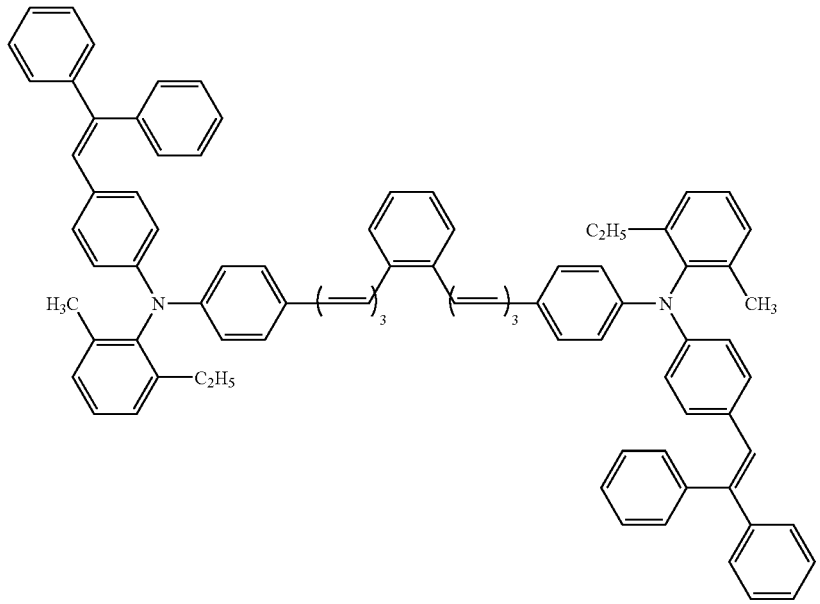

(HTM-X)

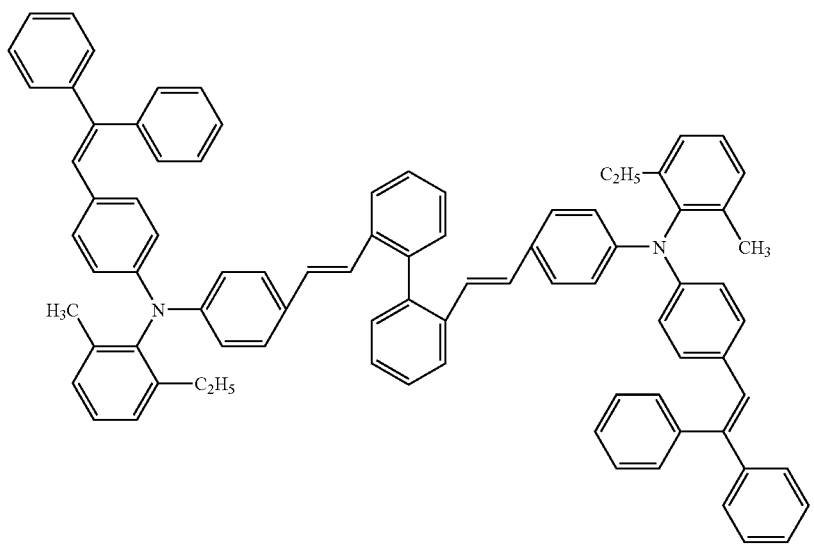

(HTM-Y)

[Second Embodiment]

A second embodiment of the invention is a process for the production of the stilbene derivative compound represented by the general formula (1) and described in the first embodiment. As shown in the following reaction formula (1) described below, it is a process for producing a stilbene derivative compound, characterized by reacting a formylated triphenylamine derivative compound represented by the general formula (4) described below with a diphosphate ester derivative compound represented by the general formula (5) described below in the presence of a catalyst.

Furthermore, in the reaction formula (1), A, plural $R^1$ to $R^7$, plural $Ar^1$ and $Ar^2$, and repeating numbers a, b, and c are the same as those defined in the general formula (1), respectively.

Reaction Formula (1)

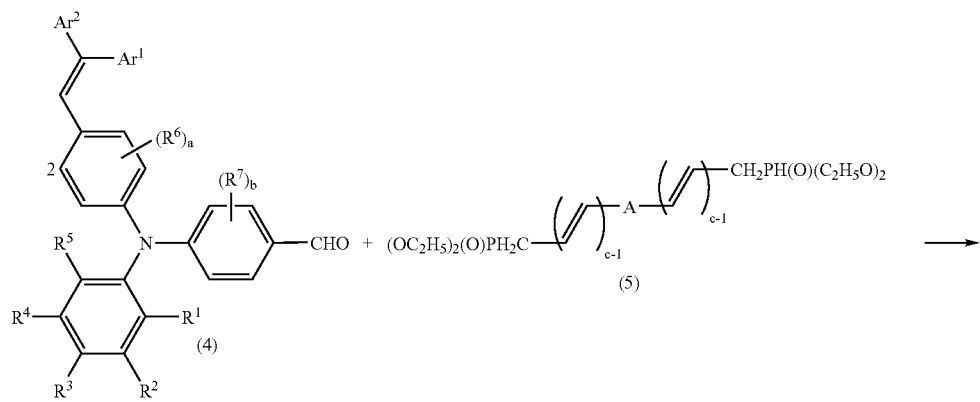

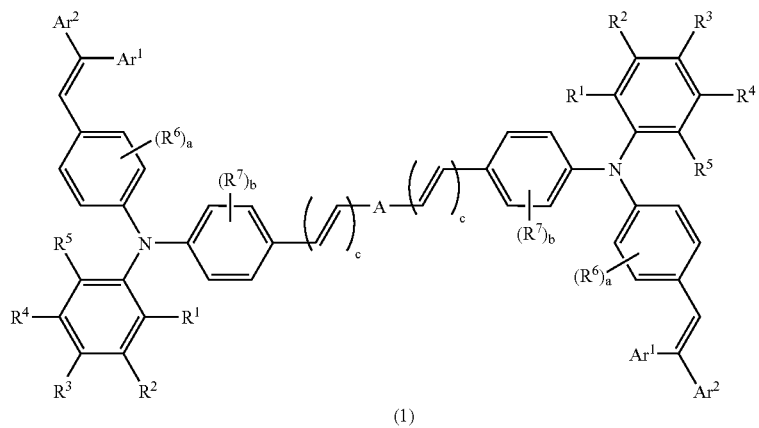

1. Synthesis of Formylated Triphenylamine Derivative Compound Represented by the General Formula (4)

First of all, for conducting the reaction formula (1), we will described a process for the synthesis of a formylated triphenylamine derivative compound represented by the general formula (4), which is provided as a raw material.

(1). Reaction Formula (4)

It is preferable to prepare the formylated triphenylamine derivative compound represented by the general formula (4) through the use of the two-stage Vilsmeier's process as fist and third steps, and the Witting's reaction as a second step.

By the way, in the reaction formula (4), A, plural $R^1$ to $R^7$, plural $Ar^1$ and $Ar^2$, repeating numbers a, b, and c are the same as those defined in the general formula (1), respectively.

Reaction Formula (4)

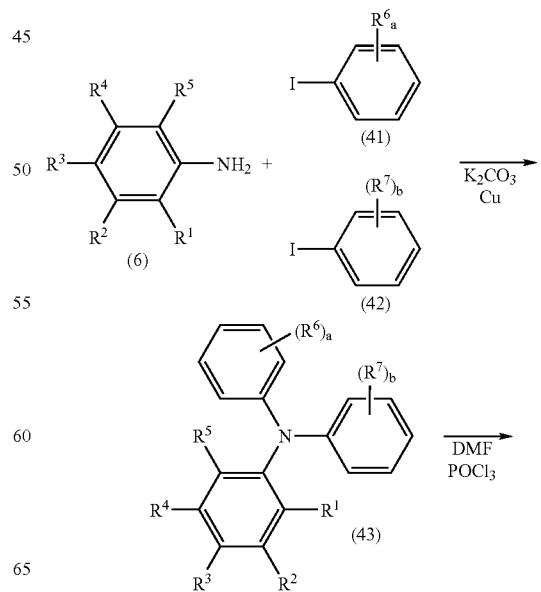

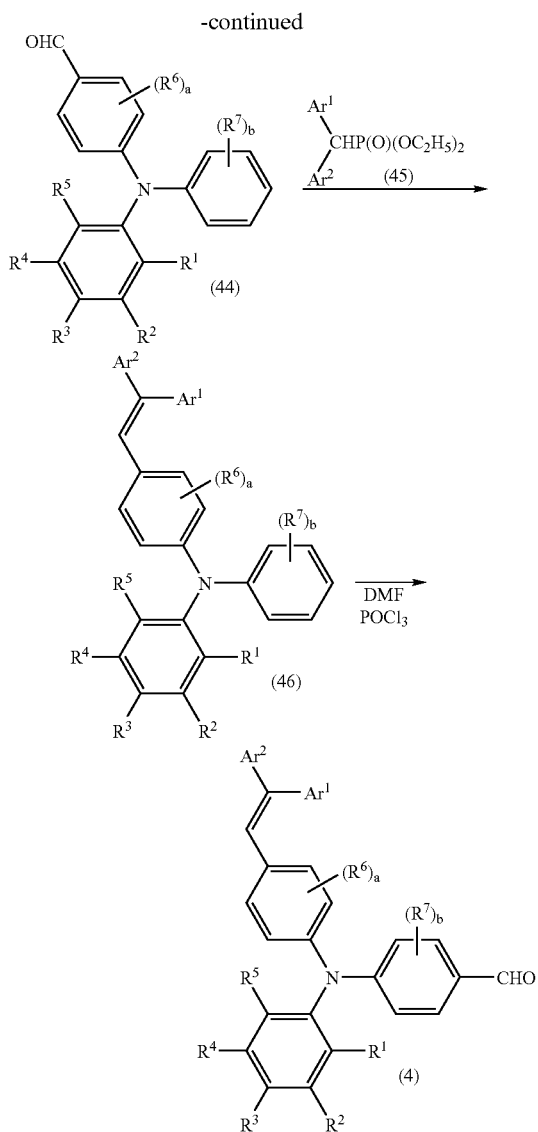

(2) First Step

Secondly, we will describe the first step in the reaction formula (4). That is, an aniline derivative compound represented by the general formula (6) is used as a raw material and reacted with two iodobenzene derivative compounds represented by the general formulas (41) and (42) to form a triphenylamine derivative compound represented by the general formula (43). Subsequently, the resulting compound was formylated by the first stage of the Vilsmeier's process. Consequently, a formylated triphenylamine derivative compound represented by the general formula (44) can be synthesized.

By the way, at the time of preparing the triphenylamine derivative compound represented by the general formula (43), it is preferable to substitute an acetyl group a hydrogen atom of one of the amino groups that constitute the aniline derivative compound represented by the general formula (6) with an acetyl group in advance. Specifically, it is preferable that part of the aniline derivative compound is protected with the acetyl group, the compound is then reacted with one of the iodobenzene derivative compounds, and a hydrogen atom is provided in parallel with removal of an acetyl group from the resulting acetylated diphenylamine derivative compound, followed by allowing the compound to react again with the other of the iodobenzene derivative compounds.

Here, for the synthesis of the triphenylamine derivative compound represented by the general formula (43), the proportion of two iodobenzene derivatives represented by the general formulas (41) and (42) (in total amount) is preferably in the range of 2 to 20 mol with respect to 1 mol of the aniline derivative compound represented by the general formula (6). This is because the amount of the desired triphenylamine derivative compound produced may decrease when the proportion of two iodobenzene derivatives added is 2 mol or less in total to 1 mol of the aniline derivative compound. On the other hand, an unreacted part of iodobenzene derivative compounds remains in large quantity when the proportion of two iodobenzene derivative compounds added exceeds 20 mol with respect to 1 mol aniline derivative compound, so that the desired triphenylamine derivative may be purified with difficulty. Furthermore, the ratio between the iodobenzene derivative compounds added, which are represented by the general formulas (41) and (42), is preferably about 1:1 in mole ratio.

Furthermore, for the reaction between the aniline derivative compound represented by the general formula (6) and two iodobenzene derivatives represented by the general formulas (41) and (42), the reaction temperature is preferably in the range of 160 to 260° C. in general, and the reaction time is preferably in the range of 2 to 30 hours. This is because these conditions for the reaction allow the desired reaction to be effectively carried out using comparatively simple production facilities.

Furthermore, a Vilsmeier reagent used in the Vilsmeier's process is preferably a combination of the following compounds (i) and (ii):

(i) a halogenating agent such as phosphorous oxychloride, phosgene, oxalyl chloride, thionyl chloride, triphenylphosphine bromine, or hexachlorotriphosphazatriene; and (ii) N,N-dimethylformamide (DMF), N-methylformanilide (MFA), N-formylmorpholine, or N,N-diisopropylformamide.

In particular, as a Vilsmeier reagent in this invention, DMF, which can be also used as a solvent, may be suitably used in combination with phosphorous oxychloride. Furthermore, zinc chloride may be added in catalytic amount to facilitate the Vilsmeier's process.

Furthermore, for preparing the Vilsmeier reagent, the proportion of the compound (ii) used to 1 mol of the compound (i) is preferably in the range of 1 to 20 mol, more preferably in the range of 1 to 5 mol.

The amount of the Vilsmeier reagent used is preferably in the range of 1 to 5 mol, more preferably in the range of 1 to 3 mol per mol of the triphenylamine derivative compound represented by the general formula (43).

Furthermore, with respect to the reaction conditions for formylating the triphenylamine derivative compound in the Vilsmeier's process, it is preferable to carry out the reaction at a temperature of 130° C. or less for a reaction time of 5 to 240 minutes.

In addition, the second stage of the Vilsmeier's process may be also carried out on the basis of the conditions of the first stage thereof.

Subsequently, a triphenylamine derivative represented by the general formula (46) is synthesized by the Witting's reaction. That is, the formylated triphenylamine derivative compound represented by the general formula (44) is reacted with a phosphorus ylid derivative compound represented by the formula (45) in the presence of n-butyllithium or the like as a catalyst.

Here, the phosphorus ylid derivative compound represented by the formula (45) is preferably added in the ratio of 1 to 3 mol per mol of the formylated triphenylamine derivative compound represented by the general formula (44) because of the following reason: The produced amount of the triphenylamine derivative compound represented by the general formula (46) may decrease when the phosphorus ylid derivative compound is added in the ratio of less than 1 mol per mol of the formylated triphenylamine derivative compound. On the other hand, when the phosphorus ylid derivative compound is added in the above ratio of 3 mol per mol of the formylated triphenylamine derivative compound, an unreacted part of the phosphorus ylid derivative compound remains in excess. Therefore the purification of the triphenylamine derivative compound represented by the general formula (46) may become difficult.

Therefore, it is preferable to add the phosphorus ylid derivative compound represented by the general formula (45) in the ratio of 1.2 to 2 mol per mol of the formylated triphenylamine derivative compound represented by the general formula (44).

For carrying out the reaction between the formylated triphenylamine derivative compound represented by the general formula (44) and the phosphorus ylid derivative compound represented by the general formula (45), in general, a preferable reaction temperature is in the range of −30 to 20° C. and a preferable reaction time is in the range of 5 to 120 minutes. This is because these conditions for the reaction allow the desired reaction to be effectively carried out using comparatively simple production facilities.

Reagents, which can be used in the Witting's process singly or in combination, include sodium alcoholate such as n-butyllithium methoxide and sodium ethoxide; and metal hydride such as sodium hydride and potassium hydride.

(4) Third Step

Next, the triphenylamine derivative compound represented by the general formula (46) is formylated by the second stage of the Vilsmeier's process, thereby obtaining a formylated triphenylamine derivative compound represented by the general formula (4).

In addition, the reaction conditions or the like for the second stage of the Vilsmeier's process in the third step is preferably based on those of the first stage of the Vilsmeier's process in the first step.

2. Diphosphate Ester Derivative Compound

Then, for carrying out the reaction formula (1), we will describe a process for the synthesis of a diphosphate ester derivative compound represented by the general formula (5) to be provided as a raw material.

That is, the diphosphate ester derivative compound represented by the general formula (5) can be synthesized as shown in the reaction formula (5) described below. In addition, "A" in the reaction formula (5) refers the same matter as that of "A" in the general formula (1), while X refers a halogen atom such as a chlorine or bromine atom.

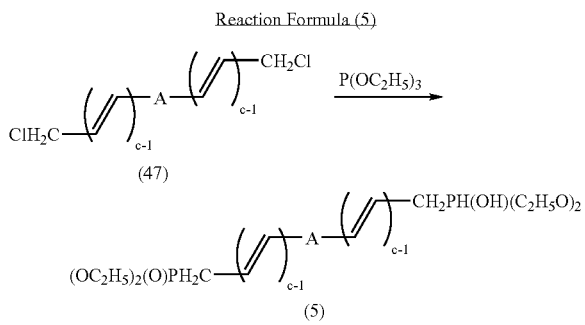

For carrying out the reaction for synthesizing the diphosphate ester derivative compound, for instance, it is preferable that triethyl phosphite is added to an inorganic solvent or an appropriate solvent and then reacted with a halogenated methyl derivative compound. This is because such a procedure allows the reaction to produce the diphosphate ester derivative compound represented by the in high yield.

Here, for initiating the synthetic reaction, the triethyl phosphate used is preferably used in the ratio of at least 2 mol, more preferably in the range of 2 to 10 mol per mol of the halogenated methyl derivative compound. In addition, generally, the reaction temperature is preferably in the range of 80 to 150° C. in general and the reaction time is preferably in the range of 2 to 10 hours.

Furthermore, solvents to be used in the synthesis of the diphosphate ester derivative compound preferably include, but not limited to as far as they do not affect on the above reaction, ethers such as diethyl ether, tetrahydrofuran, and dioxane; halogenated hydrocarbon such as methylene chloride, chloroform, and dichloroethane; aromatic hydrocarbon such as benzene and toluene; and dimethylformamide.

Moreover, for the synthesis of the diphosphate ester derivative compound, the addition of a predetermined amount of tertiary amine is preferable. This is because the tertiary amine removes halogenated alkyl from the reaction system to facilitate the reaction for the synthesis of the diphosphate ester derivative compound. Preferable tertiary amines include triethyl amine, tributyl amine, pyridine, and 4-(dimethylamino) pyridine, which may be used independently or in combination of two or more of them.

3. Reaction Conditions

Then, the reaction conditions for carrying out the reaction formula (1) will be described in detail.

That is, according to the reaction formula (1) descried above, the stilbene derivative compound represented by the general formula (1) can be synthesized under the reaction conditions described above.

Specifically, for the reaction between the formylated triphenylamine derivative compound represented by the general formula (4) and the diphosphate ester derivative represented by the general formula (5), the reaction temperature is preferably in the range of −10 to 30° C. in general and the reaction time is preferably in the range of 1 to 14 hours.

In addition, suitable solvents to be used in the reaction include, but not limited to as far as they do not affect on the reaction, include: ethers such as diethyl ether, tetrahydrofuran, and dioxane; halogenated hydrocarbon such as methylene chloride, chloroform, and dichloroethane and aromatic hydrocarbon such as benzene and toluene.

Furthermore, suitable catalysts to be used in the reaction include: sodium alcoholate such as sodium methoxide and sodium ethoxide; metal hydride such as sodium hydride and potassium hydride; and metal salt such as n-butyllithium.

Here, the amount of the catalyst added is preferably in the range of 1.0 to 1.5 mol per mol of the formylated triphenylamine derivative compound. This is because reactivity between the formylated triphenylamine derivative compound and the diphosphate ester derivative compound may deteriorate remarkably when the amount of the catalyst added is below 1.0 mol. On the other hand, if the amount of the catalyst added exceeds 1.5 mol, the reaction between the formylated triphenylamine derivative compound and the diphosphate ester derivative compound may be extremely difficult to control.

Furthermore, for allowing the reaction between the formylated triphenylamine derivative compound represented by the general formula (4) and the diphosphate ester derivative compound represented by the general formula (5), the proportion of the formylated triphenylamine derivative compound added is preferably in the range of 2 to 3 mol with respect to 1 mol of the diphosphate ester derivative compound. This is because the produced amount of the stilbene derivative compound represented by the general formula (1) tends to be decreased as the formylated triphenylamine derivative compound and the diphosphate ester derivative compound are reacted at the ratio of 1:1 when the formylated triphenylamine derivative compound is added in the below ratio of 2 mol per mol of the diphosphate ester derivative compound. In addition, if the formylated triphenylamine derivative compound is added in the above ratio of 3 mol, an unreacted part of the formylated triphenylamine derivative compound may remain to make the purification of the stilbene derivative compound difficult. Therefore, it is preferable to add the formylated triphenylamine derivative compound in the ratio of 2 to 2.5 in mole ratio with respect to 1 mol of the diphosphate ester derivative compound.

4. Production Examples

Then, as an example of the production of the stilbene derivative compound represented by the general formula (3) described in the first embodiment, we will describe an exemplified process for the production of a stilbene derivative compound as illustrated in the reaction formula (2), in which the formylated triphenylamine derivative compound described in the general formula (7) and the diphosphate ester derivative compound described in the general formula (8) in the presence of a base.

By the way, the process for producing the stilbene derivative compound represented by the reaction formula (2) is one of the embodiments of the process for producing the stilbene derivative compound represented by the reaction formula (1) ($R^8$, $R^9$, and $R^{10}$ in the reaction formula (2) describe the same matters as those described above, respectively).

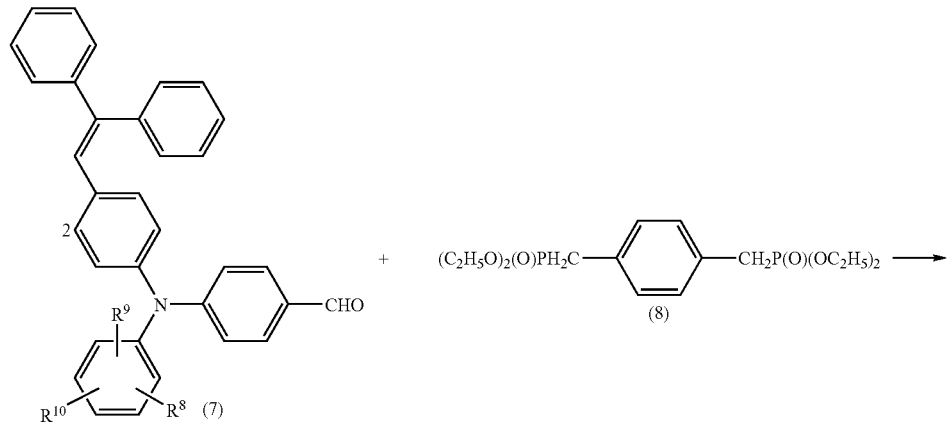

Reaction Formula (2)

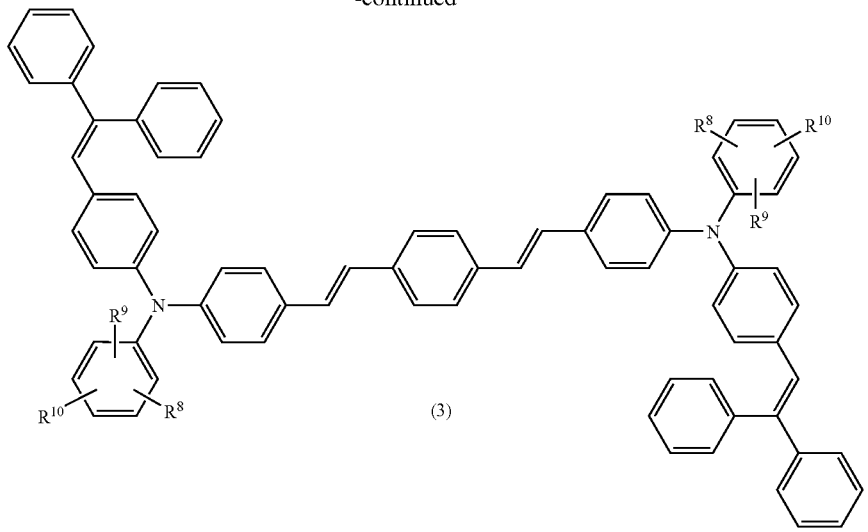

(3)

(1) Synthesis of Formylated Triphenylamine Derivative Compound

First of all, we will describe a process for the synthesis of a formylated triphenylamine derivative compound represented by the general formula (7), which can be provided as a raw material for carrying out the reaction formula (2).

Specifically, as shown in the reaction formula (3) described below, the formylated triphenylamine derivative compound is preferably synthesized using both the two-stage Vilsmeier's process and the Witting's reaction. By the way, $R^8$, $R^9$, and $R^{10}$ in the reaction formula (3) represent the same matters as those of $R^8$, $R^9$, and $R^{10}$ in the general formula (3). Besides, the reaction conditions for the Vilsmeier's process and the Witting's reaction may be the same as those described in the second embodiment.

Reaction Formula (3)

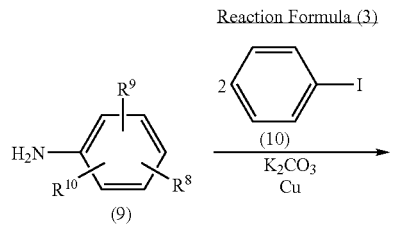

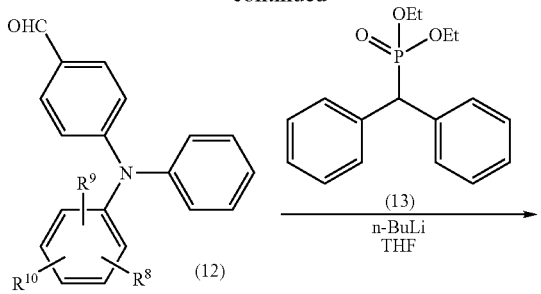

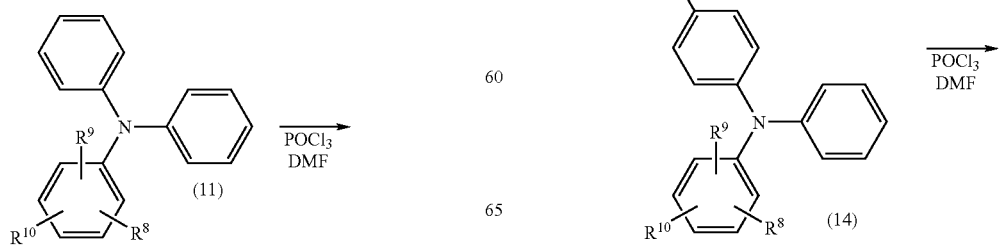

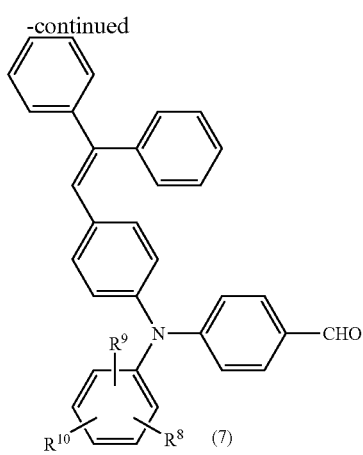

(2) Synthesis of Diphosphate Ester Derivative Compound

In addition, we will describe a process for the synthesis of a diphosphate ester derivative compound represented by the general formula (8) which can be provide as a row material for carrying out the reaction formula (2). For instance, the diphosphate ester derivative compound represented by the formula (8) may be synthesized as illustrated in the reaction formula (6) below on the basis of the conditions already described in the second embodiment. By the way, X in the reaction formula (6) is a halogen tom such as a chlorine atom or a bromine atom.

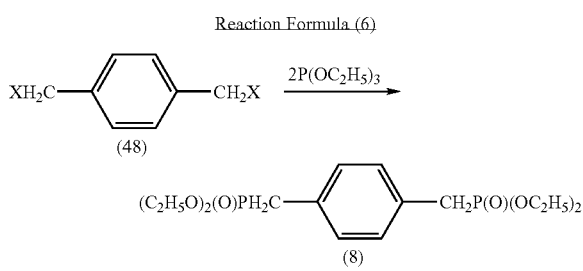

(3) Reaction Conditions

Next, according to the reaction formula (2), the stilbene derivative compound represented by the general formula (3) can be obtained. However, the reaction conditions may be the same as those already described in the second embodiment.

[Third Embodiment]

A third embodiment of the present invention is an electrophotographic photoconductor, in which a photoconductive layer is mounted on an electroconductive substrate, characterized in that the photoconductive layer contains a stilbene derivative compound represented by the general formula (1).

By the way, there are two types of electrophotographic photoconductors known in the art, monolayer type and laminated type. The stilbene derivative compound of the present invention is applicable to each of them.

In particular, however, it is preferably applied to the monolayer type in terms of: usability in each of positive and negative charge types; simplicity in structure and manufacturability; preventable film-defects caused during the layer formation; improvable optical characteristics due to a negligible boundary surface between the layers; and so on.

1. Monolayer Type Photoconductor (1) Basic Configuration

As shown in FIG. 10($a$), a monolayer type photoconductor 10 is prepared by mounting a single photoconductive layer 14 on an electroconductive substrate 12.

The photoconductive layer can be prepared by dissolving or dispersing a stilbene derivative compound (hole transporting agent) represented by the general formula (1), a charge generating agent, a binder resin, and optionally an electron transporting agent in an appropriate solvent. The coating solution thus obtained is applied on the electroconductive substrate and then dried. The characteristic features of the monolayer type photoconductor include its applicability to each of positive and negative charge types in sole configuration, simple layer configuration, and excellent productivity.

The resulting monolayer type photoconductor contains the stilbene derivative compound represented by the general formula (1), so that it can be distinguished by a decrease in residual potential and specified photosensitivity.

Furthermore, when the photoconductive layer of the monolayer type photoconductor contains an electron transporting agent, the sensitivity or the like of the photoconductor tends to be stabilized more as electrons are more effectively transmitted and received between the charge generating agent and the hole transporting agent.

(2) Charge Generating Agents

The charge generating agents to be used in the present invention include inorganic phthalocyanine, hydroxy gallium phthalocyanine, chlorogallium phthalocyanine, oxotitanyl phthalocyanine, perylene pigment, bisazo pigment, dithioketo pyrroropyrrole pigment, inorganic naphthalocyanine pigment, metal naphthalocyanine pigment, squalane pigment, tris-azo pigment, indigo pigment, and azulenium pigment, which may be used alone or in combination.

In particular, an image-forming apparatus in a digital optical system, such as a laser beam printer or a facsimile using a semiconductor layer or the like as an optical source, requires a photoconductor having sensitivity to wavelengths of 700 nm or more. Therefore, phthalocyanine pigments such as inorganic phthalocyanine and oxotitanyl phthalocyanine are suitably used.

On the other hand, an image-forming apparatus in an analog optical system, such as an electrostatic copier using a halogen lamp or the like as a white optical source, requires a photoconductor having sensitivity to the visible region. Therefore, for example, a perylene pigment or a bis-azo pigment is suitably used.

(3) Hole Transporting Agent

In addition to the stilbene derivative compound of the present invention, which is provided as a hole transporting agent, the electrophotographic photoconductor of the present invention may preferably contain any of other hole transporting agents known in the art in the photoconductive layer. The conventional agents include the conventional hole-transporting substances, nitrogen-containing cyclic compounds, and condensed polycyclic compounds, for example an oxadiazole compound such as 2,5-di(4-methylaminophenyl)-1,3,4-oxadiazole, a styryl compound such as 9-(4-diethylaminostyryl) anthracene, a carbazole compound such as polyvinyl carbazole, an organic polysilane compound, a pyrazoline compound such as 1-phenyl-3-(p-dimethylamonophenyl)pyrazoline, a hydrazone compound, a triphenylamine compound, an indole compound, an oxazole compound, an isooxazole compound, a thiazole compound, a thiadizole compound, an imidazole compound, a pyrazole compound, and a triazole compound, which may be used alone or in combination.

(4) Electron Transporting Agent

Electron transporting agents which can be used in the present invention include various kinds of compounds having high electron transporting abilities, such as the conventional electron transporting substances, malononitrile, a thiopyran compound, tetracyanoethylene, 2,4,8-trinitrothioxantone, dinitrobenzene, dinitroanthracene, dinitroacridine, nitroanthraquinone, dinitroanthraquinone, succinic anhydride, maleic anhydride, and dibromomaleic anhydride, which may be used alone or in combination.

(5) Binder Resin

A binder resin used for dispersion of each ingredient may be any of various conventional resins used in the conventional photoconductor layers, including thermoplastic resins such as a styrene-butadiene copolymer, a styrene-acrylonitrile copolymer, a styrene-maleic acid copolymer, an acryl copolymer, a styrene-acrylic acid copolymer, a polyethylene resin, an ethylene-vinyl acetate copolymer, a chlorinated polyethylene resin, a polychlorinated vinyl resin, a polypropylene copolymer, an ionomer resin, a vinyl chloride-vinyl acetate copolymer, a polyester resin, alkyd resin, a polyamide resin, a polyurethane resin, a polycarbonate resin, a polyacrylate resin, polysulfone resin, a diarylphthalate resin, a ketone resin, a polyvinylbutyral resin, a polyether resin, and a polyester resin; crosslinkable thermosetting resins such as a silicon resin, an epoxy resin, a phenol resin, a urea resin, and a melamine resin; and photo-curing resins such as epoxy acrylate and urethane acrylate. Among them, in particular, the polycarbonate resin is preferable because of its excellent transparency and thermostability in addition to excellent mechanical characteristics and compatibility to the hole transporting agent.

(6) Additives

In addition, the photoconductive layer may include various kinds of the conventional additives as far as they do not affect on the characteristic features of electrophotography, for example degradation inhibitors such as an antioxidant, a radical scavenger, a single quencher, and UV absorber, a softening agent, a plasticizer, a surface modifier, an extender, a thickener, a dispersion stabilizer, wax, an acceptor, and a donor. In addition, for improving the sensitivity of the photoconductive layer, a well-known sensitizer such as terphenyl, halonaphthoquinones, or acenaphthylene may be used together with a charge generating agent.

(7) Additional Amount

When the electrophotographic photoconductor of the present invention is of a monolayer type, the amount of a charge generating agent added is preferably in the range of 0.1 to 50 parts by weight, more preferably in the range of 0.5 to 30 parts by weight with respect to 100 parts by weight of a binder resin. In addition, the amount of a hole transporting agent added is preferably in the range of 20 to 500 parts by weight, more preferably in the range of 30 to 200 parts by weight with respect to 100 parts by weight of a binder resin. Furthermore, for including an electron transporting agent, the amount of the electron transporting agent added is preferably in the range of 5 to 100 parts by weight, more preferably in the range of 10 to 80 parts by weight with respect to 100 parts by weight of a binder resin.

(8) Structure

In addition, the photoconductive layer of the monolayer type photoconductor has a thickness of 5 to 100 μm, preferably 10 to 50 μm.

Furthermore, an electroconductive substrate, on which such a photoconductive layer is to be formed, may be prepared from any of various materials having electrical conductivity, for example metals such as iron, aluminum, copper, tin, platinum, silver, vanadium, molybdenum, chromium, cadmium, titanium, nickel, palladium, indium, stainless steel, brass; plastic materials deposited or laminated with the metals; and glass coated with tin oxide, indium oxide, or the like.

Moreover, as far as the electroconductive substrate itself or the surface thereof has electrical conductivity, the electroconductive substrate may be in the form of a sheet, drum, or the like so as to fit to the configuration of an image-forming apparatus to be used. Besides, the electroconductive substrate is preferably one having a sufficient mechanical strength in use. For making a photoconductive layer on the substrate by a coating process, for example, the charge generating agent, the charge transporting agent, and the binder resin are mixed together with an appropriate solvent to prepare a dispersion solution by dispersing and mixing them with the conventional means such as a roll mill, a ball mill, an attritor, a paint shaker, or an ultrasonic dispersing device. Then, the resulting dispersion liquid may be applied and dried using the conventional means.

Furthermore, the monolayer type photoconductor may be configured as shown in FIG. 10(b) as far as the characteristics of the photoconductor are not prevented. That is, it may be configured as a photoconductor 10' provided with a barrier layer 16 between an electroconductive substrate 12 and a photoconductive layer 14. Alternatively, as shown in FIG. 10(c), it may be configured as a photoconductor 10" provided with a protective layer 18 formed on the surface of a photoconductive layer 14.

(9) Production Process

The process for manufacturing the electrophotographic photoconductor of the present invention is not specifically limited. However, it is preferable to prepare a coating liquid at first. Then, according to the conventional production process, the coating liquid obtained is applied on an electroconductive substrate (aluminum tubular material) by a dip-coating method, followed by hot-air drying at 100° C. for 30 minutes, thereby obtaining an electrophotographic photoconductor having a photoconductive layer with a predetermined film thickness.

A solvent used for preparing the coating liquid may be any of various organic solvents including alcohols such as methanol, ethanol, isopropanol, and butanol, aliphatic hydrocarbons such as n-hexane, octane, and cyclohexane, benzene, tolunene, xylene, and dimethylformaldehyde, which may be used alone or in combination.

For improving the dispersibility of charge transporting agent and charge generating agent and also improving the surface smoothness of a photoconductive layer, a leveling agent or the like may be used.

2. Laminated Type Photoconductor

As shown in FIG. 11(a), a laminated type photoconductor 20 is prepared as follows: On an electroconductive substrate 12, a charge generating layer 24 containing a charge generating agent is formed by means of deposition, coating, or the like. Then, a charge transporting layer 22 is formed by coating on the charge generating layer 24 with a coating liquid that contains a binder resin and at least one of stilbene derivative compounds (hole transporting agent) represented by the general formula (1) and drying the liquid.

In addition, the order of lamination in the above configuration may be reversed as shown in FIG. 11(b). A photoconductor 20' is provided such that the charge transporting layer 22 is formed on the electroconductive substrate 12 and then the charge generating layer 24 is formed thereon.

In this case, however, the charge generating layer 24 is extremely thinner than the charge transporting layer 22. For protecting such a layer, it is preferable to form the charge transporting layer 22 on the charge generating layer 24 as shown in FIG. 11(a).

In this case, furthermore, the same kinds of the charge generating agent, hole transporting agent, electron transporting agent, binder agent, or the like as those of the monolayer type photoconductor may be used.

In the charge generating layer, however, the amount of the charge generating agent added is preferably in the range of 5 to 1,000 parts by weight, more preferably in the range of 30 to 500 parts by weight with respect to 100 parts by weight of the binder resin. Also, when the charge generating layer contains a hole transporting agent, the amount of the hole transporting agent added is preferably in the range of 10 to 500 parts by weight, more preferably in the range of 50 to 200 parts by weight with respect to 100 parts by weight of the binder resin.

Furthermore, in the charge transporting layer, as a hole transporting agent, the amount of the stilbene derivative compound of the present invention added is preferably in the range of 10 to 500 parts by weight, more preferably in the range of 25 to 200 parts by weight with respect to 100 parts by weight of the binder resin. Moreover, when the charge transporting layer contains an electron transporting agent, the amount of the electron transporting agent added is preferably in the range of 5 to 200 parts by weight, more preferably in the range of 10 to 100 parts by weight with respect to 100 parts by weight of the binder resin.

Furthermore, the laminated type photoconductor can be of a negatively or positively charged type depending on the order of forming the charge generating layer and the charge transporting layer and the kind of the charge transporting agent used in the charge transporting layer. For example, the photoconductor is of a negatively charged type when it is prepared such that, as described above, the charge generating layer is formed on the electroconductive substrate and then the charge transporting layer is formed thereon, while the stilbene derivative of the present invention (hole transporting agent) is used as a charge transporting agent in the charge transporting layer. In this case, the charge generating layer may contain the electron transporting agent.

In the laminated type photoconductor, the photoconductive layer is constructed of the charge generating layer in a thickness of about 0.01 to 5 µm, preferably about 0.1 to 3 µm and the charge transporting layer 22 in a thickness of about 2 to 100 µm, preferably 5 to 50 µm.

[Fourth Embodiment]

A fourth embodiment of the present invention is an image-forming apparatus, which is distinguished by comprising the electrophotographic photoconductor (hereinafter, also simply referred to as a photoconductor) of the third embodiment and the charge, exposure, development, and transfer stages are respectively arranged around the electrophotographic photoconductor to carry out image formation. Such a configuration of the image-forming apparatus allows the formation of distinct images for long periods of time. Here, the exemplified image-forming apparatus will be described on the assumption that a monolayer type photoconductor is used as an electrophotographic photoconductor.

Thus, for carrying out an image-forming process of the fourth embodiment, a copying machine 30 (i.e., an image-forming apparatus) shown in FIG. 12 can be suitably used. The copying machine 30 comprises an image-forming unit 31, a delivery unit 32, an image-reading unit 33, and an original-feeding unit 34. Furthermore, the image-forming unit 31 comprises an image-forming part 31a and a sheet-feeding part 31b. In the example, as shown in the figure, the original-feeding unit 34 includes an original-mounting tray 34a, an original-feeding mechanism 34b, and an original-delivery tray 34c. The original mounted on the original-mounting tray 34a is transferred to an image-reading position through the original-feeding mechanism 34b and then ejected therefrom onto the original-delivery tray 34c.

Subsequently, when the original reaches to the original-reading position P, the image-reading unit 33 reads an image on the original using light emitted from an optical source 33a. Specifically, an optical element 33b such as CCD is employed to form image signals corresponding to the image information of the original.

On the other hand, recording sheets (hereinafter, simply referred to as sheets) S stacked on the sheet-feeding part 31b are transferred one by one to the image-forming part 31a on which a photoconductor drum 41 is provided as an image bearing member. In addition, around the photoconductor drum 41, a charger 42, an exposure device 43, a developing device 44, a transfer roller 45, and a cleaning device 46 are arranged along the rotary direction of the drum 41.

Among these components, the photoconductor drum 41 is provided with a rotary motion in the direction indicated by the solid-line arrow in the figure and the surface thereof is uniformly charged by the charger 42. After that, the exposure device 43 carries out an exposure process on the photoconductor drum 41 on the basis of the image signals described above, thereby forming an electrostatic latent image on the surface of the photoconductor drum 41. Depending on the electrostatic latent image, the developing device 44 allows toner to attach on the surface of the photoconductor drum 41 and then carries out development to make a toner image on that surface. Then, the toner image is transferred as a transfer image to a sheet S fed to a nip portion between the photoconductor drum 41 and the transfer roller 45. Subsequently, the sheet S on which the transfer image has been transferred is transferred to a fixing unit 47 and subjected to a fixing process.

The image-fixed sheet S is transferred to the delivery unit 32 or optionally subjected to a post processing (e.g., a staple processing). The post processing is carried out after transferring the sheet S to an intermediate tray 32a. After that, the sheet S is ejected to a delivery tray part (not shown) provided on the side of the image-forming apparatus. On the other hand, when no post processing is required, the sheet S is directly ejected to the delivery tray 32b provided below the intermediate tray 32a. By the way, both the intermediate tray 32a and the delivery tray 32b are constructed as the so-called inner-body delivery part.

Furthermore, after carrying out the transfer as described above, residual toner (and paper powder) remained on the photoconductor drum 41 is removed by the cleaning device 46. In other words, the photoconductor drum 41 is cleaned while the residual toner is collected into a disposal toner container (not shown).

EXAMPLES

Example 1

(1) Synthesis of Stilbene Derivative Compound (1)-1 Synthesis of Triphenylamine Derivative Compound The synthesis of a triphenylamine derivative compound represented by the general formula (50) described below was carried out according the reaction formula (7) described below.

That is, in a two-neck flask of 500 ml in volume, 152.0 g anhydrous sodium carbonate (1.10 mol) and 9.5 g powdery copper (0.15 mol) were added and then heated for 2 hours while stirring to uniform. Subsequently, after cooling to room temperature, the solution was added with 67.6 g of an aniline compound (0.5 mol) represented by the formula (49) described below and 305.9 g of iodobenzene (1.5 mol) and then heated again to 220° C. to allow the reaction for 2.5 hours. After that, the solution was cooled to room temperature and then added with 100 ml toluene, followed by filtration. The resulting residue was dissolved in toluene and dried over activated clay. After that, the residue was dissolved in toluene and then added with methanol to crystallization. Then, the residue was dissolved in toluene again and added with methanol to crystalline and the resulting residue was followed by filtration and dried to form crystal. Subsequently, the resulting crystal was purified through silica gel column chromatography (developing solvent: chloroform/hexane solvent), thereby obtaining 79.3 g of a triphenylamine derivative compound represented by the general formula (50) (yields: 55.2%).

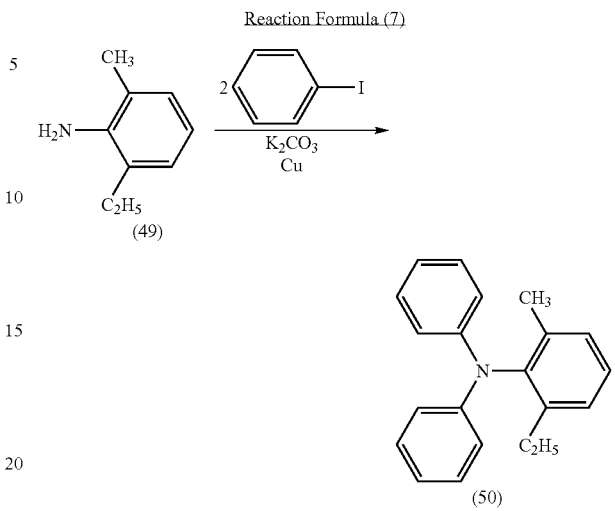

(1)-2 Synthesis of Formylated Triphenylamine Derivative Compound

The synthesis of a formylated triphenylamine derivative compound represented by the general formula (51) described below was carried out according the reaction formula (8) described below.

That is, 60 g of a triphenylamine derivative compound (0.21 mol) represented by the general formula (50), 450 ml of dimethylformamide (DMF), and 41.8 g of phosphorous oxide chloride (0.27 mol) were placed in a 500-ml flask and then heated at 85° C. or more and stirred for 3 hours. After completion of reaction, the reaction solution was dropped into 600 ml ion-exchanged water and the precipitated solid was then separated through filtration. The resulting solid was washed with ion-exchanged water while stirring. After that, the solid was dissolved in toluene and the organic layer was then washed five times with ion-exchanged water. After that, the resulting organic layer was added with anhydrous sodium sulfate and activated clay, followed by drying and absorptive treatment. Subsequently, the toluene was distilled off under reduced pressure and the residue was then dissolved in 200 ml toluene, followed by crystallization with methanol. Consequently, 51.4 g of a formylated triphenylamine derivative compound represented by the general formula (51) (yields: 77.6%).

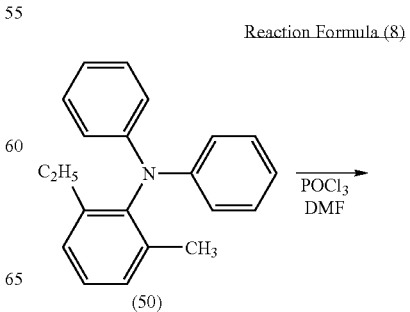

-continued

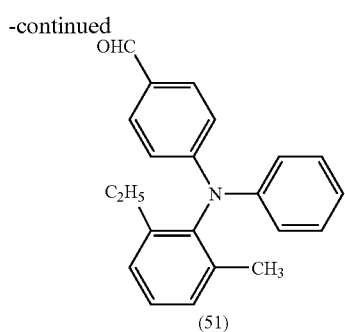

(1)-3 Synthesis of Phosphorus Ylid

The synthesis of phosphorus ylid represented by the general formula (13) was carried out according to the reaction formula (9) described below.

That is, 150 g α-bromodiphenylmethane (0.61 mol) and 121 g triethanol phosphoric acid (0.72 mol) were added and heated at 210° C., followed by stirring for 1 hour. Subsequently, after cooling to room temperature, it was subjected to purification with vacuum distillation. The resulting residue was purified through silica gel column chromatography (developing solvent: ethyl acetate solvent) thereby obtaining 168.4 g of phosphorus ylid represented by the general formula (13) (yields: 90.7%).

Reaction Formula (9)

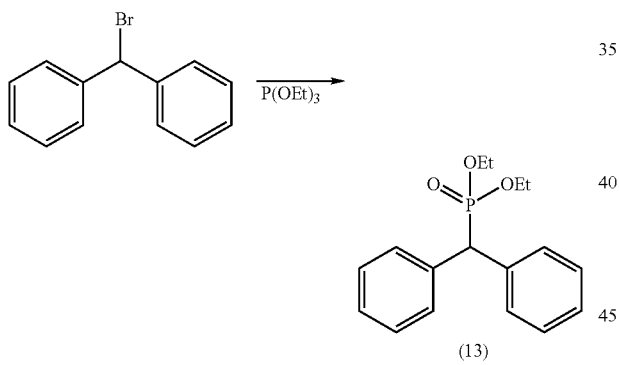

(1)-4 Synthesis of Triphenylamine Derivative Compound

The synthesis of a triphenylamine derivative compound represented by the formula (52) described below was carried out according the reaction formula (10) described below.

That is, in a four-neck flask of 1000 ml in volume, 25 g phosphorus ylid (0.082 mol) represented by the general formula (13) was added. Then, the flask was subjected to substitution with argon gas and provided with 100 ml THF, followed by allowing the reaction at 5° C. or less. Subsequently, 51.2 ml n-BuLi (1.6 M in hexane solution) was dropped in the reaction solution, followed by stirring at 7° C. or less for 30 minutes. Furthermore, a solution prepared by dissolving 18 g of a formylated triphenylamine derivative compound (0.057 mol) represented by the formula (51) in 45 ml THF was dropped in the reaction solution, followed by stirring at 6° C. or less for 30 minutes. The reaction solution was added with 500 ml ion-exchanged water and then subjected to extraction with toluene. Furthermore, the resulting organic layer was washed five times with ion-exchanged water, followed by drying and absorptive treatment over anhydrous magnesium sulfate and activated clay. After that, the organic solvent was distilled off and the residue was then left standing overnight at normal temperature for two days. The precipitated solid was separated through filtration with petroleum ether and the resulting solid was then dried under reduced pressure. The resulting solid was purified through column chromatography (developing solvent: chloroform/hexane solvent), thereby obtaining 21.4 g of a triphenylamine derivative compound represented by the general formula (52) (yields: 80.6%).

Reaction Formula (10)

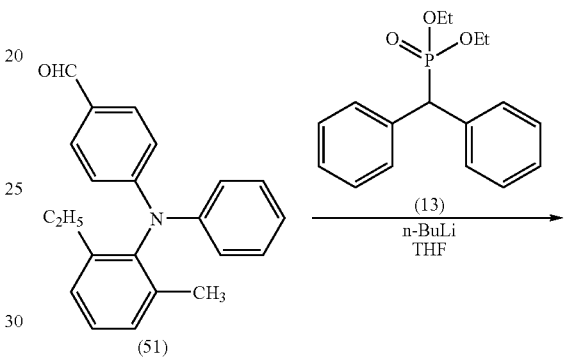

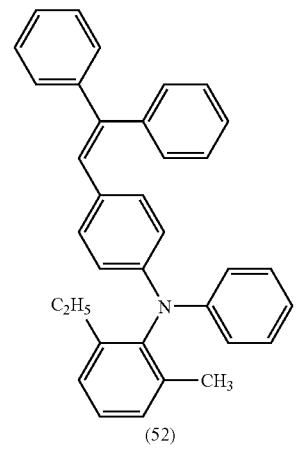

(1)-5 Synthesis of Formylated Triphenylamine Derivative Compound

The synthesis of a formylated triphenylamine derivative compound represented by the general formula (53) described below was carried out according to the reaction formula (11) described below.

That is, 20 g of a triphenylamine derivative compound (0.043 mol) represented by the general formula (52), 300 ml dimethylformamide (DMF), and 8.6 g phosphorous oxide chloride (0.06 mol) were placed in a 500-ml flask and stirred at 95° C. for 3 hours. Subsequently, 500 ml ion-exchanged water was poured into the reaction solution and the precipitated crystal was then separated through filtration. The resulting solid was washed two times with ion-exchanged water. Furthermore, the resulting crystal was dissolved in toluene and the organic layer obtained was then washed five times with ion-exchanged water. Then, the organic layer was added with anhydrous magnesium sulfate and activated clay to dry and carry out absorptive treatment, followed by distilling the solvent of under reduced pressure. The resulting residue was purified through silica gel column chromatography (developing solvent: chloroform solvent), thereby obtaining 17.8 g of a formylated triphenylamine derivative compound represented by the general formula (53) (yields: 84.0%).

triethyl phosphite (0.78 mol) were placed in a 500-ml flask and refluxed over 8 hours. After that, it was cooled and the precipitated crystal was then separated through filtration. Subsequently, the crystal was washed with n-hexane and then recrystallized with chloroform/n-hexane, thereby obtaining 98.1 g of a diphosphate ester derivative compound represented by the general formula (8) (yields: 86.4%).

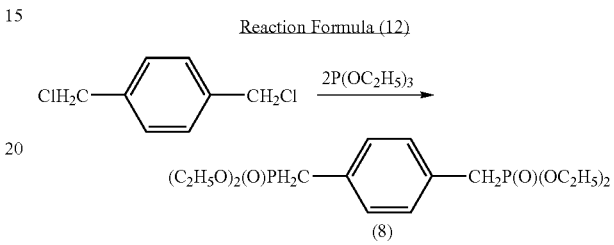

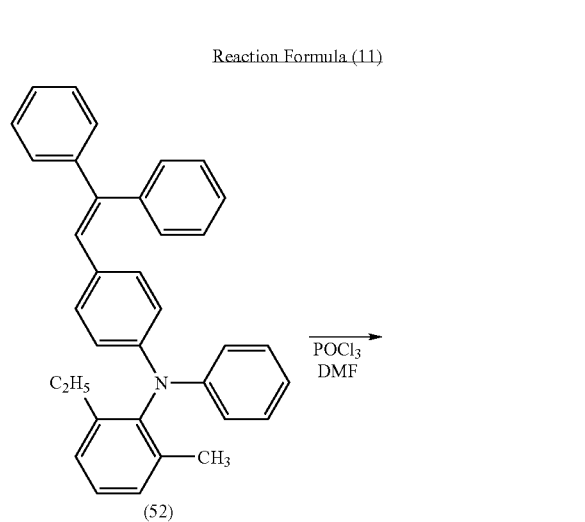

(1)-6 Synthesis of Diphosphate Ester Derivative Compound

The synthesis of a diphosphate ester derivative compound represented by the general formula (8) was carried out according the reaction formula (12) described below. That is, 52.5 g 1,4-bis(chloromethyl)benzene (0.3 mol) and 130 g (1)-7 Synthesis of Stilbene Derivative Compound The synthesis of a stilbene derivative compound represented by the general formula (16) was carried out according the reaction formula (13) described below.

That is, in a two-neck flask of 500 ml in volume, 6.8 g diphosphate ester (0.018 mol) represented by the general formula (8) and obtained in (1)-6 was added. After substitution with argon, 50 ml THF and 8.3 g NaOMe (0.043 mol)/30 ml THF were added and stirred for 30 minutes. Subsequently, in this flask, 18 g of the formylated triphenylamine derivative compound (0.036 mol) represented by the above formula (53) was dissolved and then stirred at room temperature for about 12 hours. After that, ion-exchanged water was poured into the reaction solution and the water layer was then neutralized with dilute hydrochloric acid. Subsequently, it was subjected to extraction with toluene and the resulting organic layer was then washed five times with ion-exchanged water. Then, the organic layer was dried over anhydrous magnesium sulfate to distill the solvent off. The resulting residue was purified through silica gel chromatography (developing solvent: chloroform/hexane), thereby obtaining 14.6 g of a stilbene derivative compound represented by the general formula (16) (yields: 76.5%).

Figure 1:
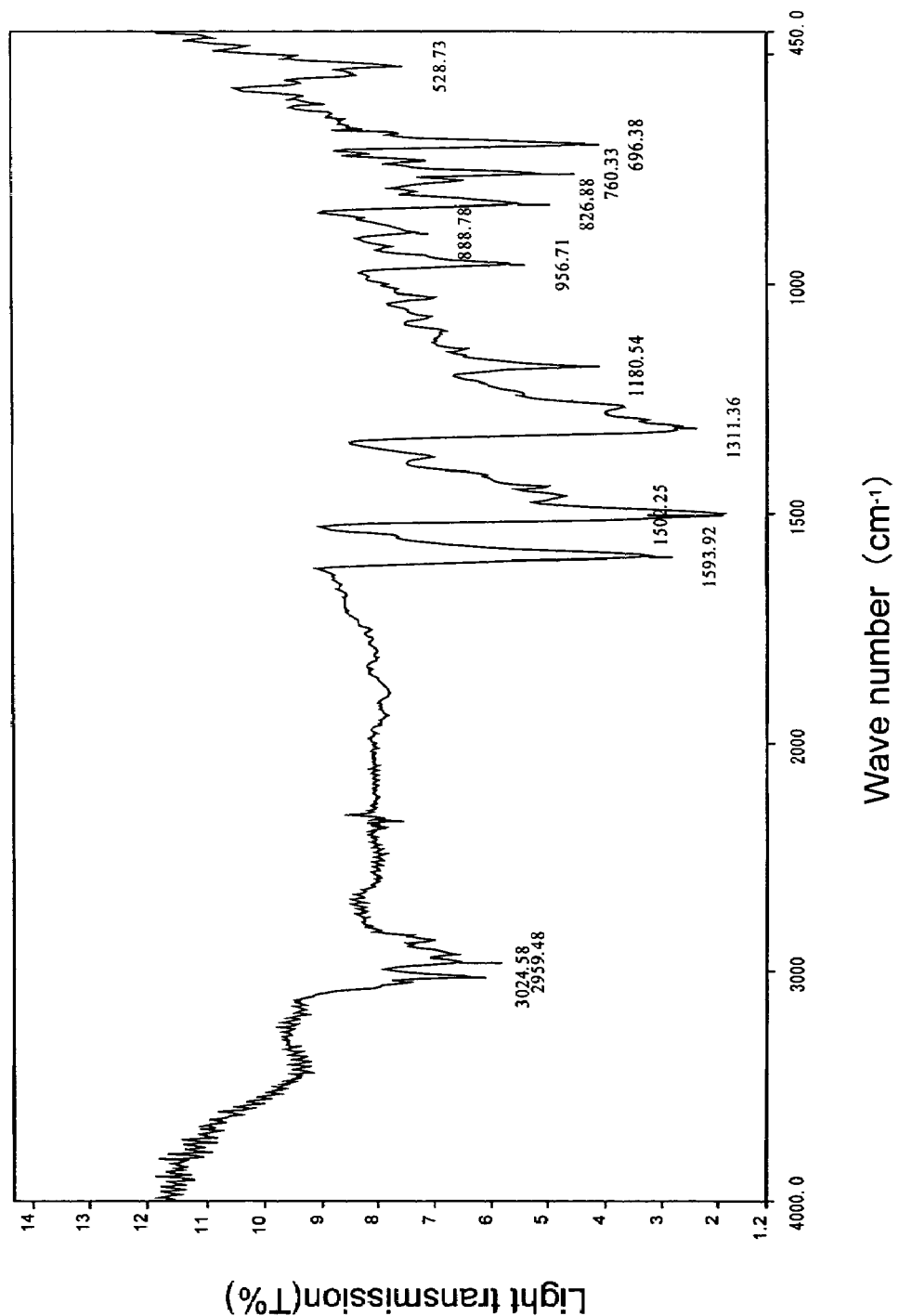
FIG. 1 is a diagram provided for illustrating the infrared spectroscopic (IR) chart of a stilbene derivative compound represented by the formula (16).
Figure 2:
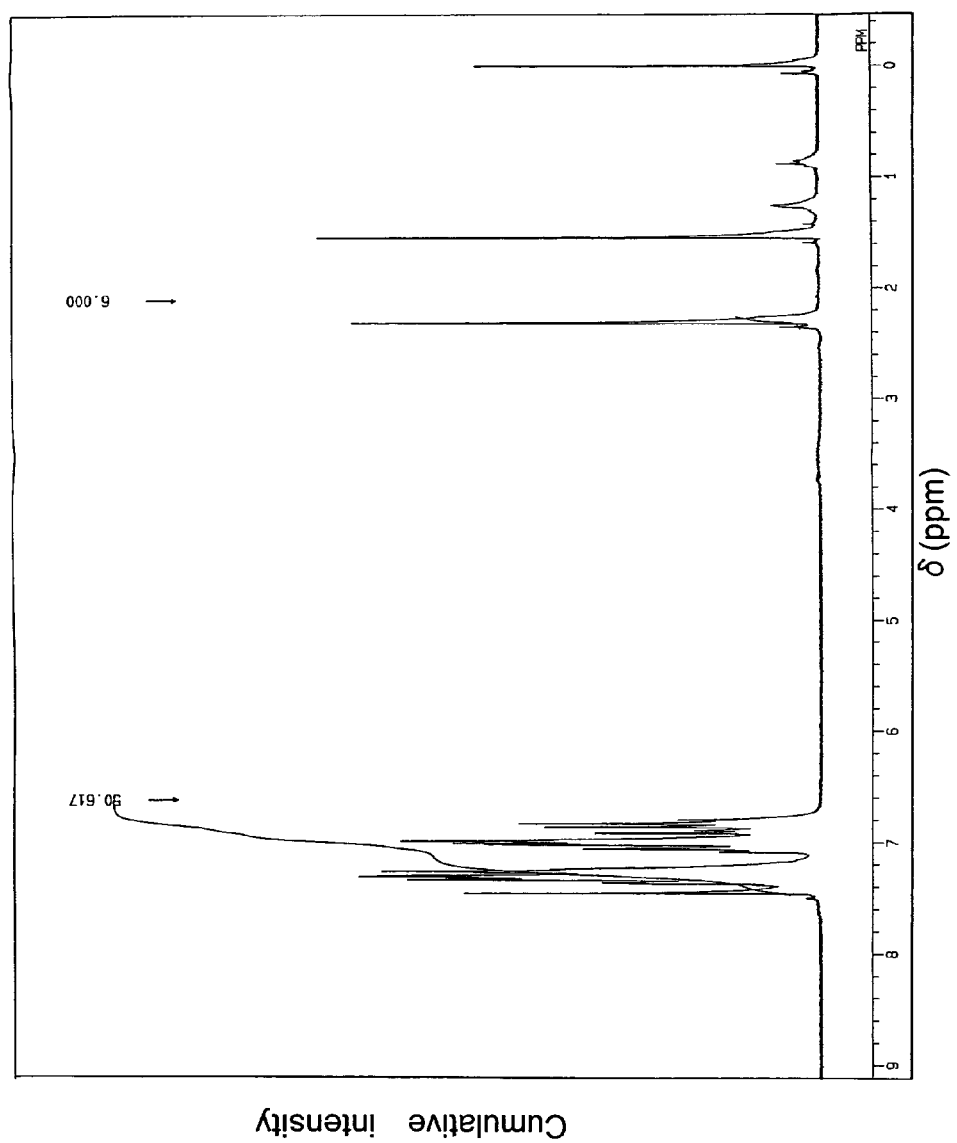
FIG. 2 is a diagram provided for illustrating the proton-NMR chart of the stilbene derivative compound represented by the formula (16).
Figure 3:
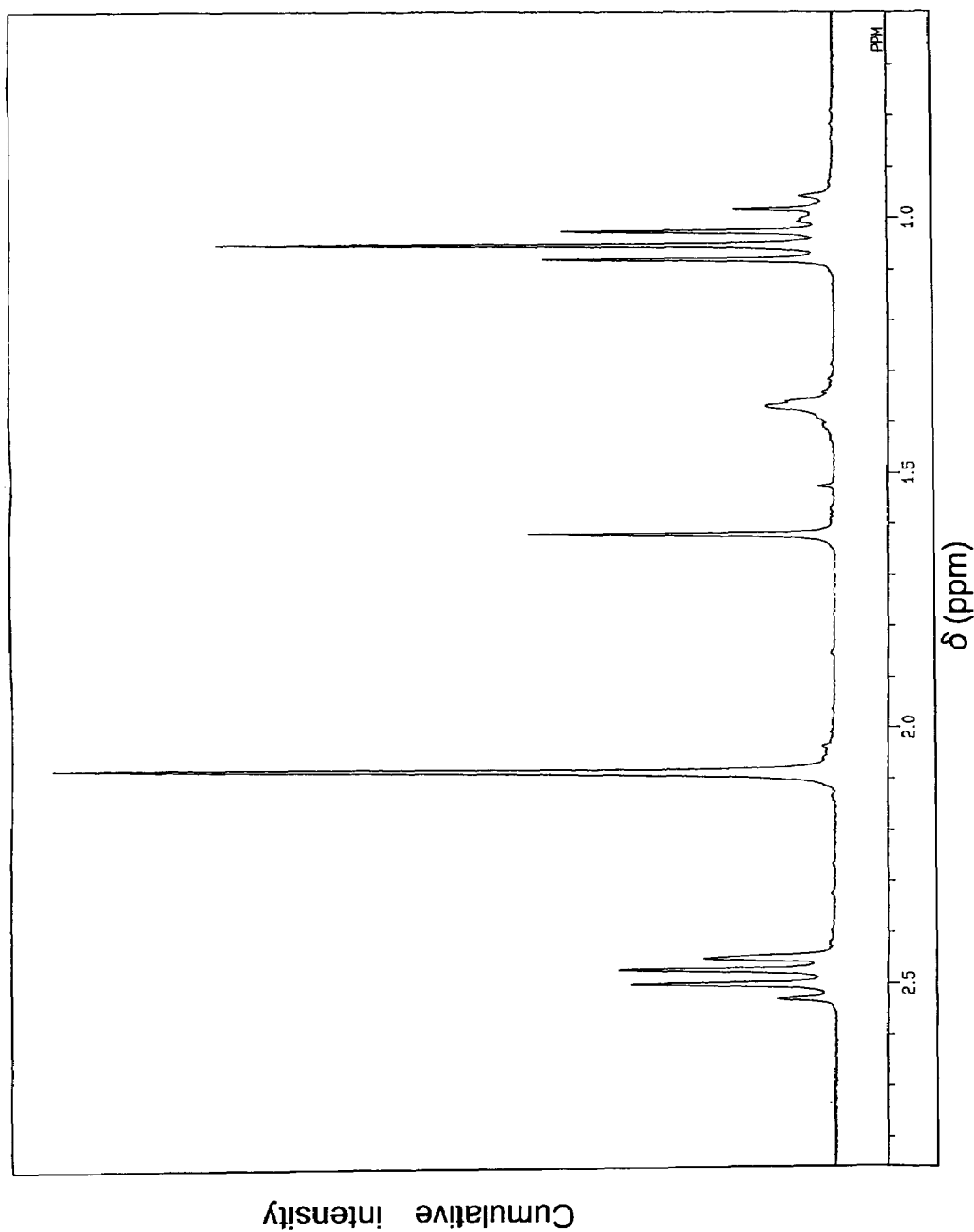
FIG. 3 is a diagram (1) provided for illustrating an enlarged proton-NMR chart of the stilbene derivative compound represented by the formula (16).
Figure 4:
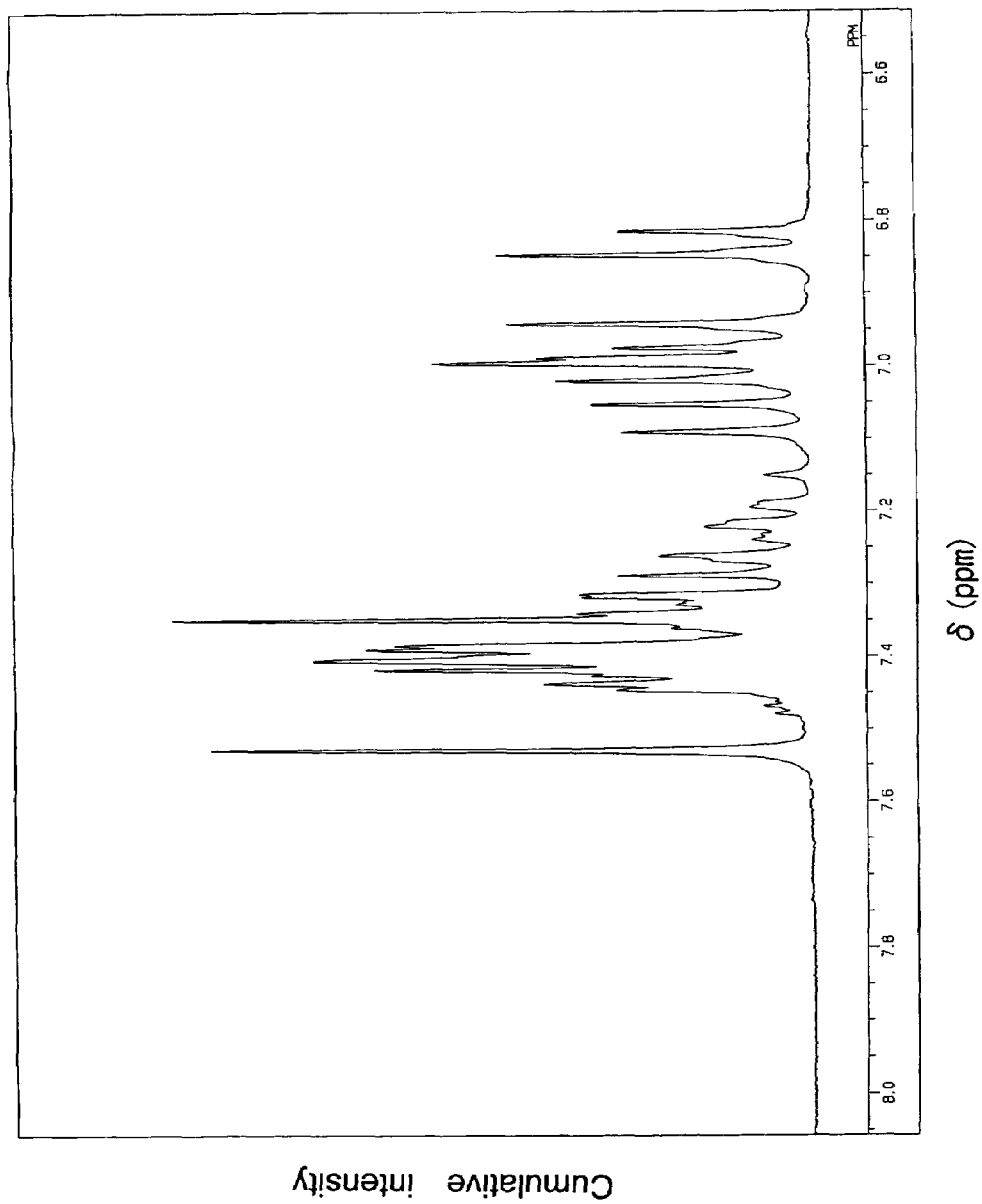
FIG. 4 is a diagram (2) provided for illustrating an enlarged proton-NMR chart of the stilbene derivative compound represented by the formula (16).

An infrared absorption spectrum of the resulting stilbene derivative compound is shown in FIG. 1 and proton-NMR charts (an overall view and two enlarged views) thereof are shown in FIGS. 2, 3, and 4, respectively.

Reaction Formula (13)

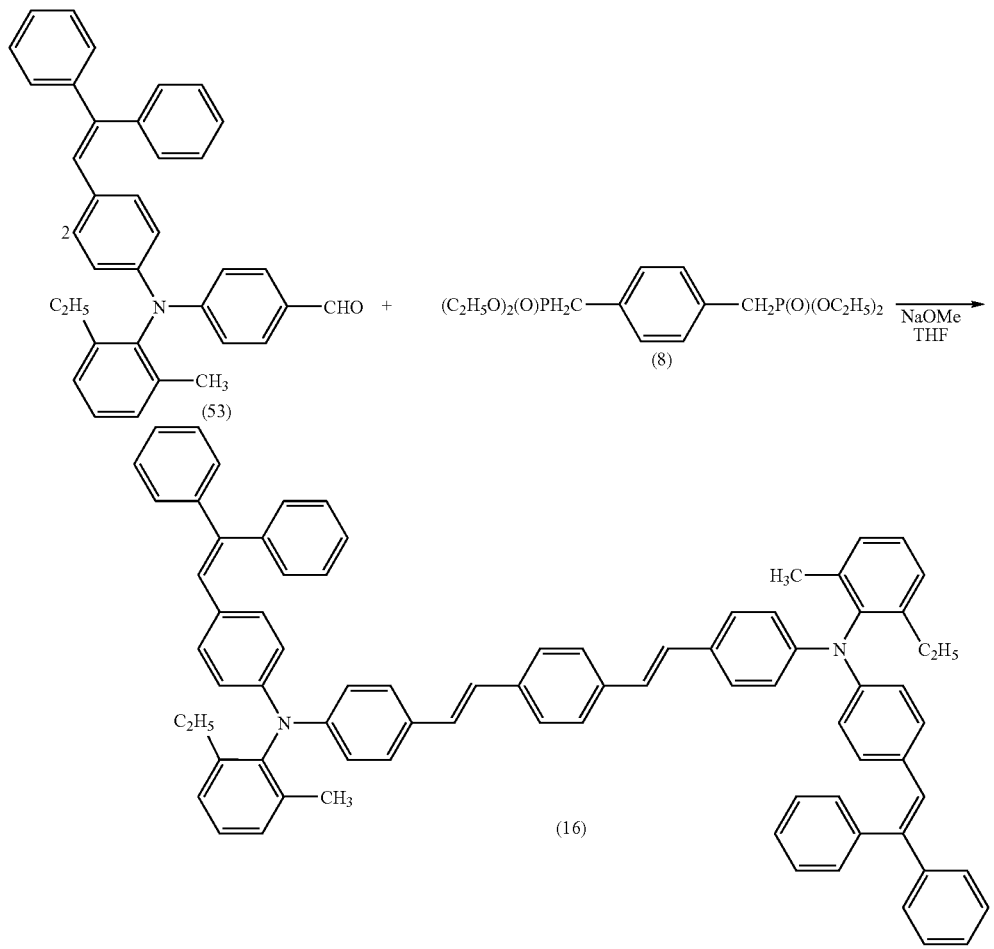

(2) Evaluation (2)-1 Preparation of Electrophotographic Photoconductor and Measurements of Initial Surface Potential, Half Decay Exposure, and Residual Potential A monolayer type electrophotographic photoconductor was prepared using the stilbene derivative compound obtained as a hole transporting agent. Then, the initial surface potential, half decay exposure, and residual potential of the photoconductor were determined, respectively. That is, in 800 parts by weight of tetrahydrofuran provided as a solvent, there were added 60 parts by weight of the obtained stilbene derivative compound (HTM-A), which was provided as a hole transporting agent; 5 parts by weight of X-type nonmetal phthalocyanine (CGM-A) represented by the general formula (54) described below, which was provided as a charge generating agent; and 100 parts by weight of a polycarbonate resin (Resin-A) having a viscosity-average molecular weight of 50,000 represented by the general formula (55) described below, which was provided as a binder resin, respectively. Subsequently, these compounds were mixed and dispersed using a ball mill for 50 hours to prepare a coating liquid for a monolayer type photoconductive layer. The resulting coating liquid was applied on an electroconductive substrate (aluminum tubular material) by a dip-coating method, followed by hot-air drying at 100° C. for 30 minutes, thereby obtaining an electrophotographic photoconductor having a monolayer type photoconductive layer with a film thickness of 25 μm.

Next, the initial electric properties of the obtained electrophotographic photoconductor, i.e., initial charging potential ($V_O$), half decay exposure ($E_{1/2}$), and residual potential ($V_R$) were measured. At first, using a drum-sensitivity testing machine (manufactured by GENTEC Co., Ltd.), the photoconductor was charged so as to have a surface potential of 710 V. For the half decay exposure ($E_{1/2}$), we measured the time period required for reducing the surface potential by half with exposure to monochromatic light (half bandwidth: 20 nm and light intensity: 1.5 μJ/cm$^2$) of 780 nm in wavelength, which was obtained from light emitted from a halogen lamp through a band pass filter. For the residual potential (VR), the surface potential at the time after lapse of 330 msec. from the initiation of exposure was measured and defined as a residual potential.

The results of the respective measurements are listed in Table 1. The obtained electrophotographic photoconductor was confirmed to have a small residual potential and predetermined sensitivity. In Tale 1, furthermore, X-type nonmetal phthalocyanine provided as a charge generating agent is represented by CGM-A (hereinafter, the same is applied).

(2)-2 Evaluation on Crystallinity

After the application of the photoconductive layer, the electrophotographic photoconductor was dried naturally for 1 hour before hot-air drying. Then, the external appearance of the electrophotographic photoconductor was visually observed and the crystallinity thereof was evaluated on the basis of the following criteria;

very good: Crystallization is not observed at all.
good: Crystallization is hardly observed
fair: Crystallization is observed a little.
bad: Crystallization is observed remarkably.

The obtained results are listed in Table 1.

(2)-3 Evaluation on Repetitive Charging Property

The electrophotographic photoconductor prepared in (2)-1 was mounted on a electro-static process printer (FS-1000, manufactured by Kyocera Corporation + a modified machine) and then the surface potential thereof was set to about 450 V. After that, 5,000 sheets were continuously printed out. Subsequently, the surface potential of the photoconductor was measured again and defined as a post-printing surface potential. In addition, the difference between the posit-printing surface potential and the initial measured value (450 V) was defined as a charging variation. The results are listed in Table 1.

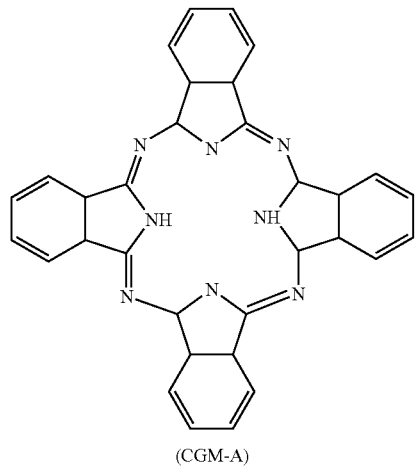

(CGM-A)

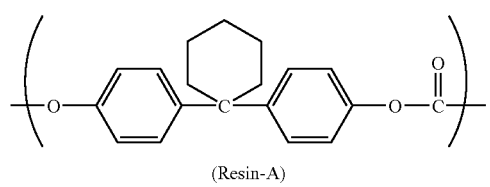

(Resin-A)

Examples 2 to 4

In Examples 2 to 4, monolayer type photoconductive layers were prepared and evaluated just as in the case of Example 1, respectively, except that quinone derivative compounds (ETM-A to C) represented by the formulas (56), (57), and (58) were employed as their respective electron transporting materials and each of which was added in an amount of 30 parts by weight in the coating liquid of Example 1.

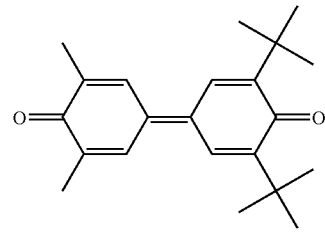

(ETM-A)

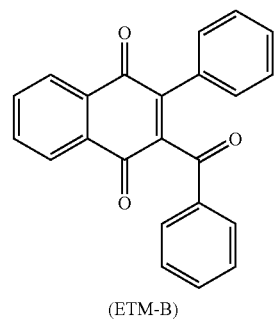

(ETM-B)

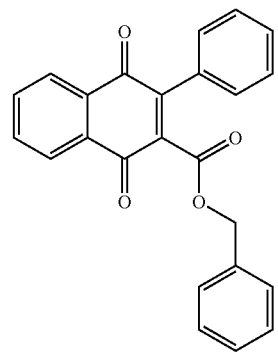

(ETM-C)

Examples 5 to 18

In each of Examples 5 to 18, a monolayer type photoconductor was prepared and evaluated just as in the case of Example 1, except that the kind of the hole transporting agent in Example 1 or the like was changed to another one as shown in Table 1.

Comparative Examples 1 to 14

In Comparative Examples 1 to 14, as shown in Table 1, monolayer type photoconductors were prepared and evaluated just as in the case of Example 1 or the like, respectively, except that stilbene derivative compounds represented by the formulas (59) to (63) described below were employed instead of the hole transporting agent in Example 1 or the like.

(59)
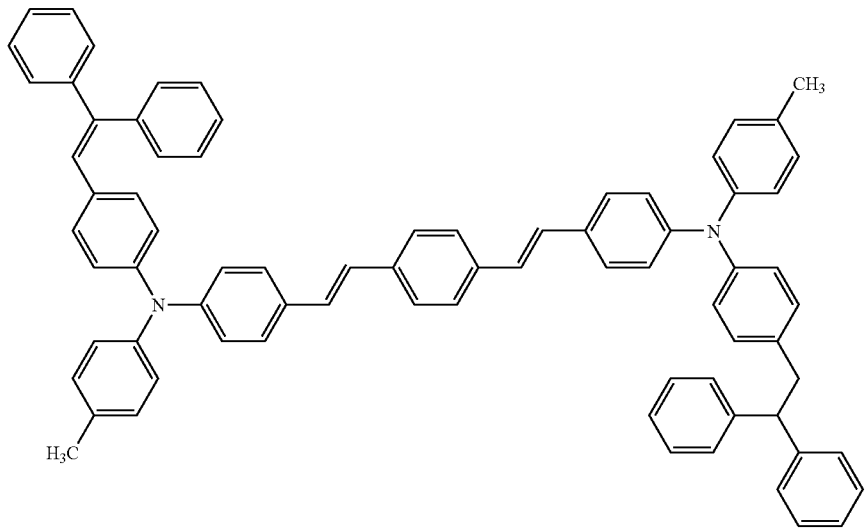
(HTM-Z)
(60)
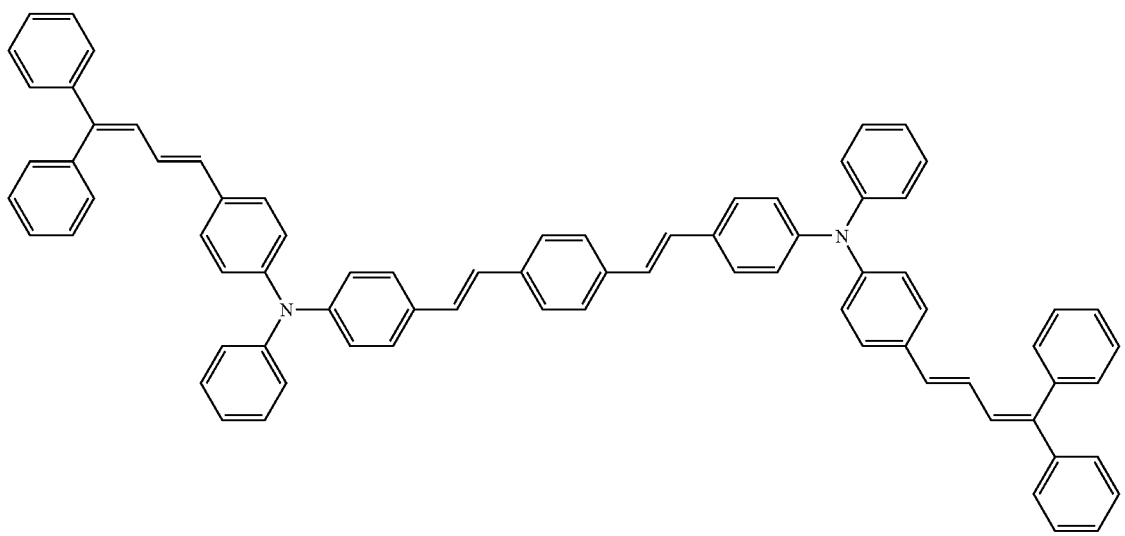
(HTM-AA)
(61)
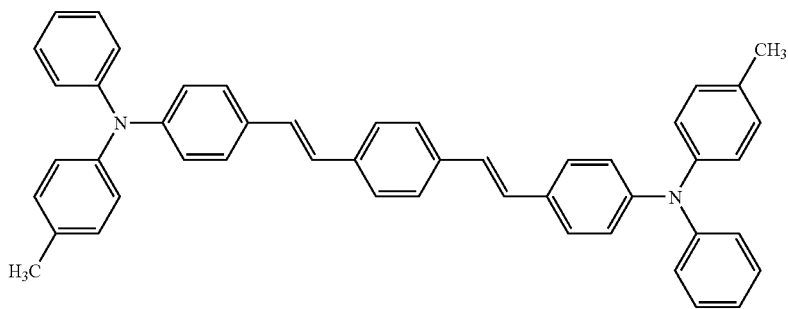
(HTM-AB)

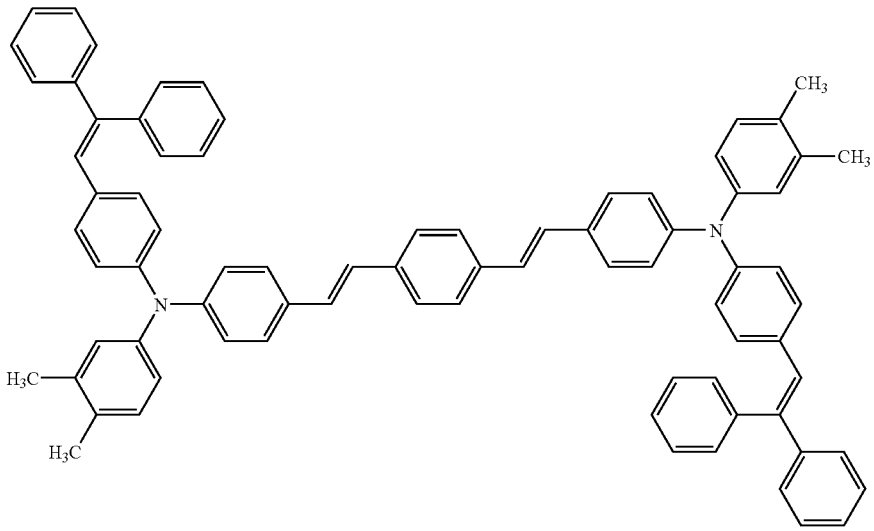

(HTM-AC)

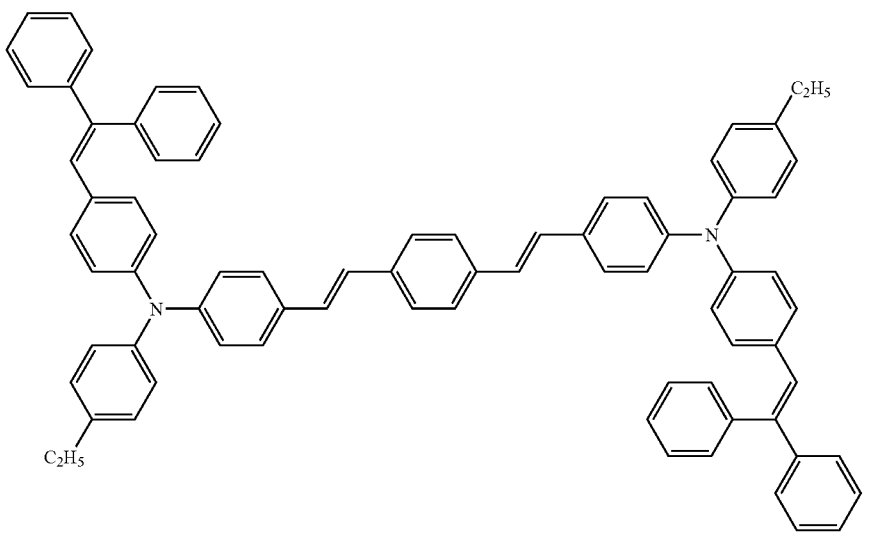

(HTM-AD)

TABLE 1

| | CHARGE GENERATING AGENT | HOLE TRANSPORTING AGENT | CHARGE TRANSPORTING AGENT | $V_o$ (V) | $V_r$ (V) | $E_{1/2}$ (sec.) | CRYSTAL-LIZATION | CHARGING VARIATION (V) |
|---|---|---|---|---|---|---|---|---|
| EXAMPLE 1 | CGM-A | HTM-A | — | 704 | 98 | 0.89 | very good | 23 |
| EXAMPLE 2 | CGM-A | HTM-A | ETM-A | 701 | 90 | 0.83 | very good | 17 |
| EXAMPLE 3 | CGM-A | HTM-A | ETM-B | 702 | 92 | 0.84 | very good | 16 |
| EXAMPLE 4 | CGM-A | HTM-A | ETM-C | 700 | 90 | 0.82 | very good | 14 |
| EXAMPLE 5 | CGM-A | HTM-B | ETM-A | 704 | 91 | 0.85 | very good | 18 |
| EXAMPLE 6 | CGM-A | HTM-C | ETM-A | 702 | 92 | 0.87 | very good | 16 |
| EXAMPLE 7 | CGM-A | HTM-D | ETM-A | 701 | 90 | 0.84 | very good | 17 |
| EXAMPLE 8 | CGM-A | HTM-E | ETM-A | 700 | 93 | 0.86 | very good | 15 |
| EXAMPLE 9 | CGM-A | HTM-F | — | 701 | 107 | 0.98 | very good | 21 |
| EXAMPLE 10 | CGM-A | HTM-F | ETM-A | 704 | 91 | 0.92 | very good | 18 |
| EXAMPLE 11 | CGM-A | HTM-F | ETM-B | 702 | 89 | 0.90 | very good | 17 |
| EXAMPLE 12 | CGM-A | HTM-F | ETM-C | 703 | 93 | 0.91 | very good | 15 |
| EXAMPLE 13 | CGM-A | HTM-G | — | 701 | 103 | 1.17 | very good | 20 |
| EXAMPLE 14 | CGM-A | HTM-G | ETM-A | 701 | 90 | 1.03 | very good | 16 |
| EXAMPLE 15 | CGM-A | HTM-G | ETM-B | 705 | 89 | 1.00 | very good | 14 |
| EXAMPLE 16 | CGM-A | HTM-G | ETM-C | 701 | 91 | 1.01 | very good | 14 |
| EXAMPLE 17 | CGM-A | HTM-H | ETM-A | 701 | 95 | 0.92 | good | 25 |

TABLE 1-continued

| | CHARGE GENERATING AGENT | HOLE TRANSPORTING AGENT | CHARGE TRANSPORTING AGENT | $V_o$ (V) | $V_r$ (V) | $E_{1/2}$ (sec.) | CRYSTAL-LIZATION | CHARGING VARIATION (V) |
|---|---|---|---|---|---|---|---|---|
| EXAMPLE 18 | CGM-A | HTM-I | ETM-A | 700 | 98 | 0.91 | good | 24 |
| COMPARATIVE EXAMPLE 1 | CGM-A | HTM-Z | — | 705 | 103 | 0.89 | bad | 40 |
| COMPARATIVE EXAMPLE 2 | CGM-A | HTM-Z | ETM-A | 700 | 89 | 0.82 | bad | 35 |
| COMPARATIVE EXAMPLE 3 | CGM-A | HTM-Z | ETM-B | 701 | 90 | 0.85 | bad | 33 |
| COMPARATIVE EXAMPLE 4 | CGM-A | HTM-Z | ETM-C | 703 | 88 | 0.85 | bad | 32 |
| COMPARATIVE EXAMPLE 5 | CGM-A | HTM-AA | — | 702 | 158 | 1.31 | bad | 42 |
| COMPARATIVE EXAMPLE 6 | CGM-A | HTM-AA | ETM-A | 702 | 147 | 1.22 | bad | 37 |
| COMPARATIVE EXAMPLE 7 | CGM-A | HTM-AA | ETM-B | 706 | 146 | 1.22 | bad | 35 |
| COMPARATIVE EXAMPLE 8 | CGM-A | HTM-AA | ETM-C | 702 | 148 | 1.21 | bad | 34 |
| COMPARATIVE EXAMPLE 9 | CGM-A | HTM-AB | — | 700 | 163 | 1.25 | bad | 40 |
| COMPARATIVE EXAMPLE 10 | CGM-A | HTM-AB | ETM-A | 701 | 153 | 1.15 | bad | 37 |
| COMPARATIVE EXAMPLE 11 | CGM-A | HTM-AB | ETM-B | 703 | 155 | 1.14 | bad | 35 |
| COMPARATIVE EXAMPLE 12 | CGM-A | HTM-AB | ETM-C | 702 | 157 | 1.12 | bad | 31 |
| COMPARATIVE EXAMPLE 13 | CGM-A | HTM-AC | ETM-A | 700 | 97 | 0.93 | bad | 36 |
| COMPARATIVE EXAMPLE 14 | CGM-A | HTM-AD | ETM-A | 699 | 96 | 0.90 | bad | 35 |

Example 19

In Example 19, according to Example 1, a stilbene derivative compound (HTM-J) represented by the general formula (25) was prepared as illustrated in the reaction formulas (14) to (19) described below and then similarly evaluated.

Reaction Formula (14)

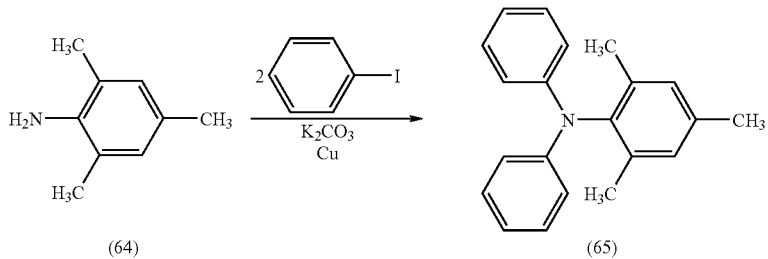

Reaction Formula (15)

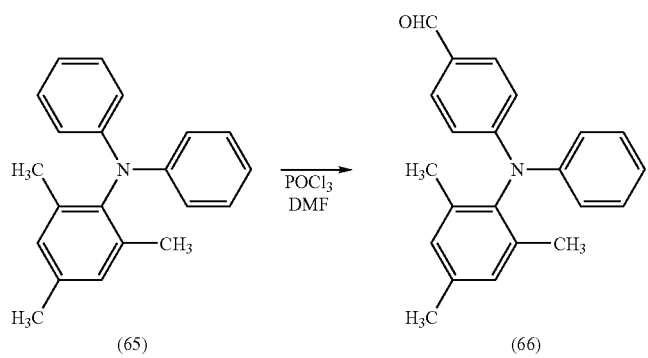

Reaction Formula (16)
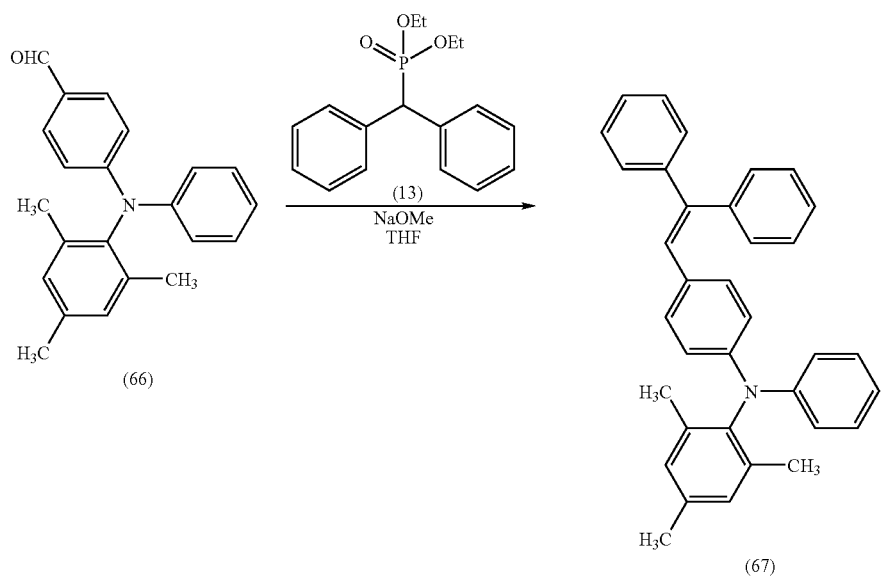
Reaction Formula (17)
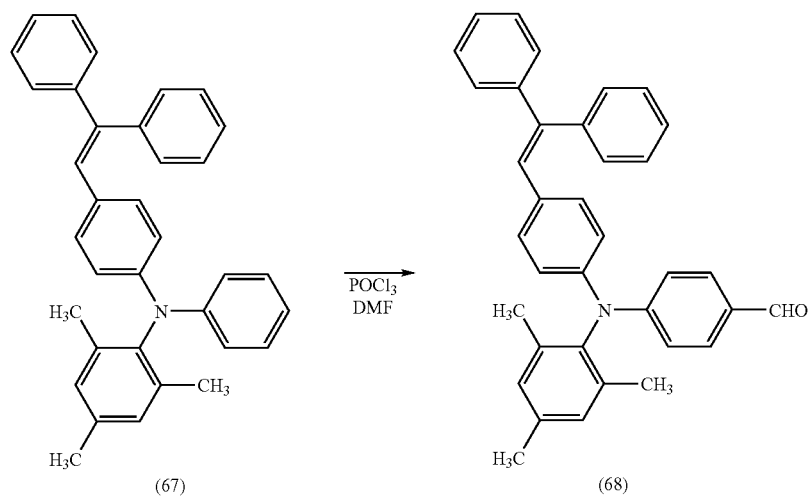
Reaction Formula (18)
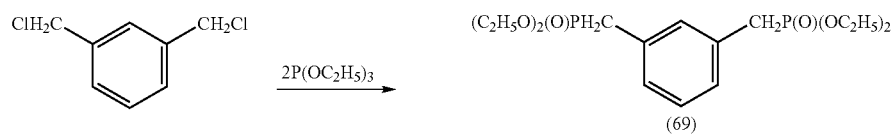

Reaction Formula (19)

-continued

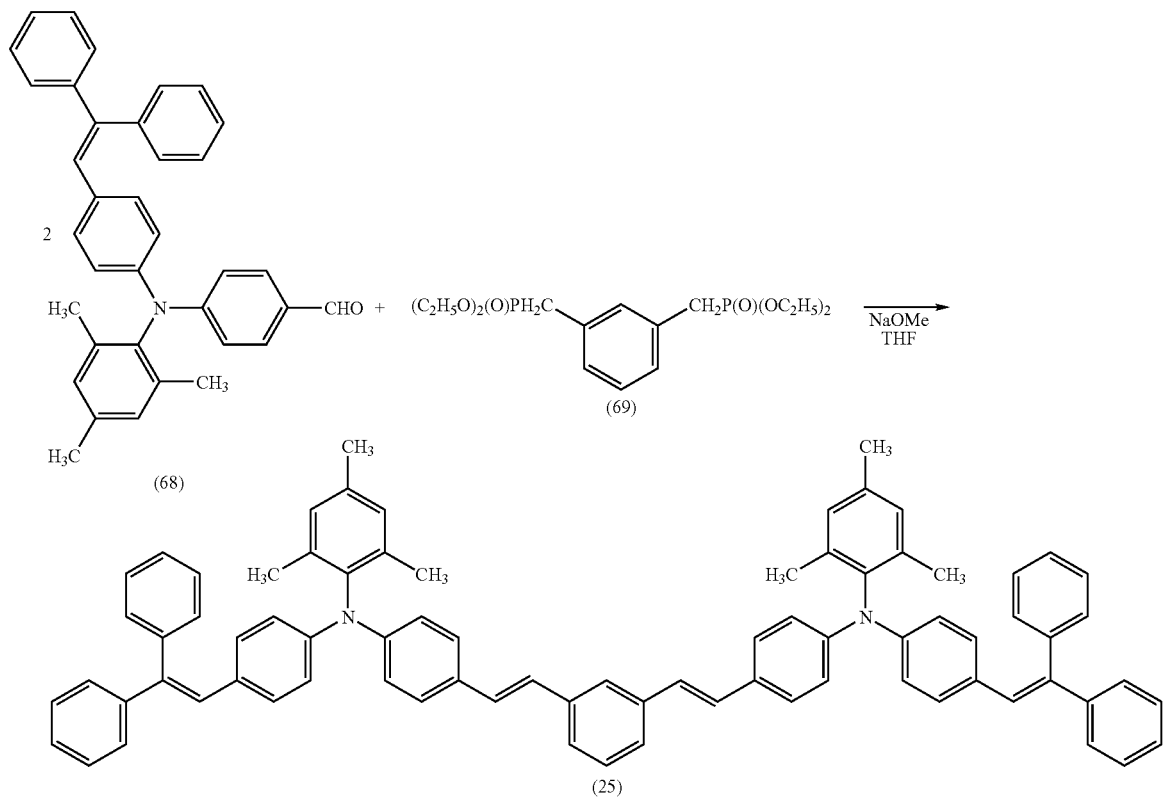

Examples 20 to 38

In Examples 20 to 38, monolayer type photoconductive layers were prepared and evaluated just as in the case of Example 2 and so on, respectively, except that the kinds of the electron transporting materials and the kinds of the hole transporting materials were different from those of Example 2 and so on as shown in Table 2.

Comparative Examples 15 to 24

In Comparative Examples 15 to 24, monolayer type photoconductive layers were prepared and evaluated just as in the case of Example 19 and so on, respectively, except that the hole transporting materials were replaced with stilbene derivative compounds represented by the formulas (70) to (73) described below as shown in Table 2.

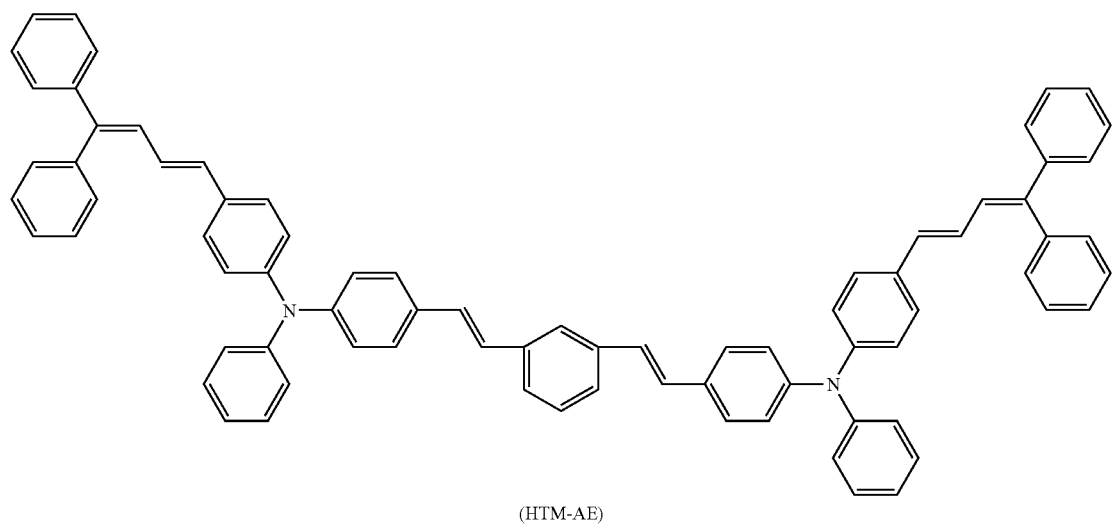

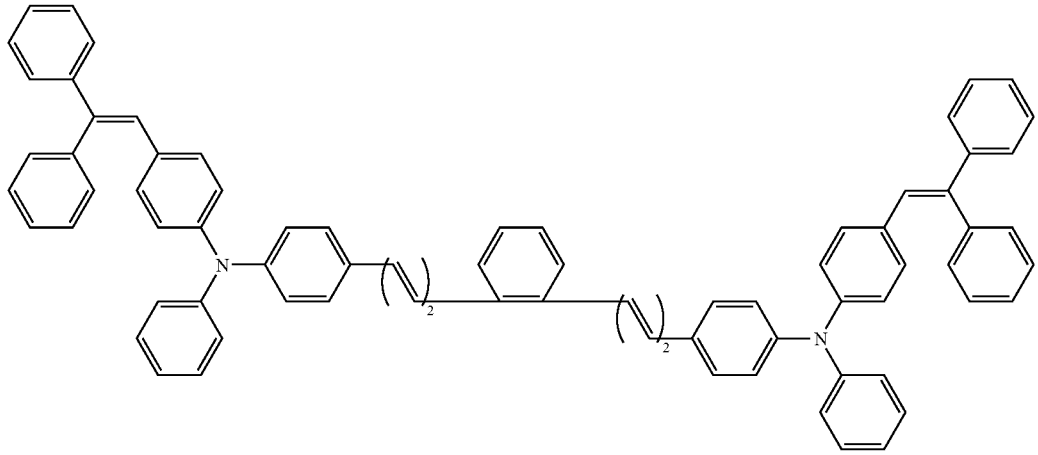
(HTM-AF) (71)
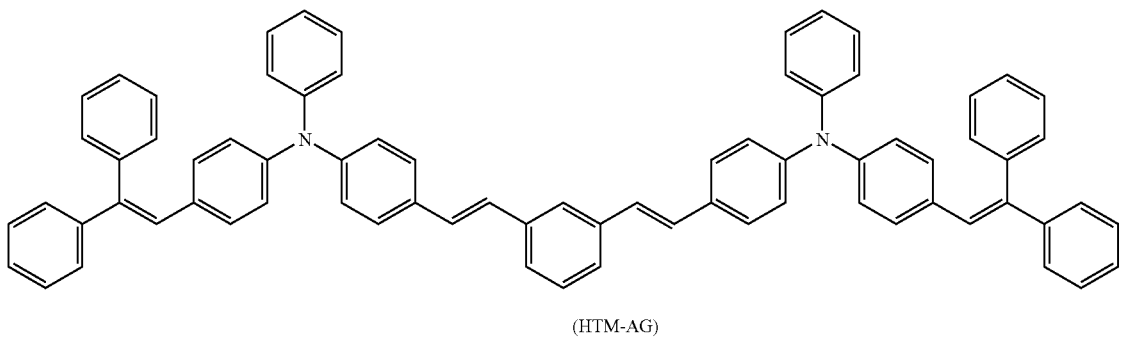
(HTM-AG) (72)
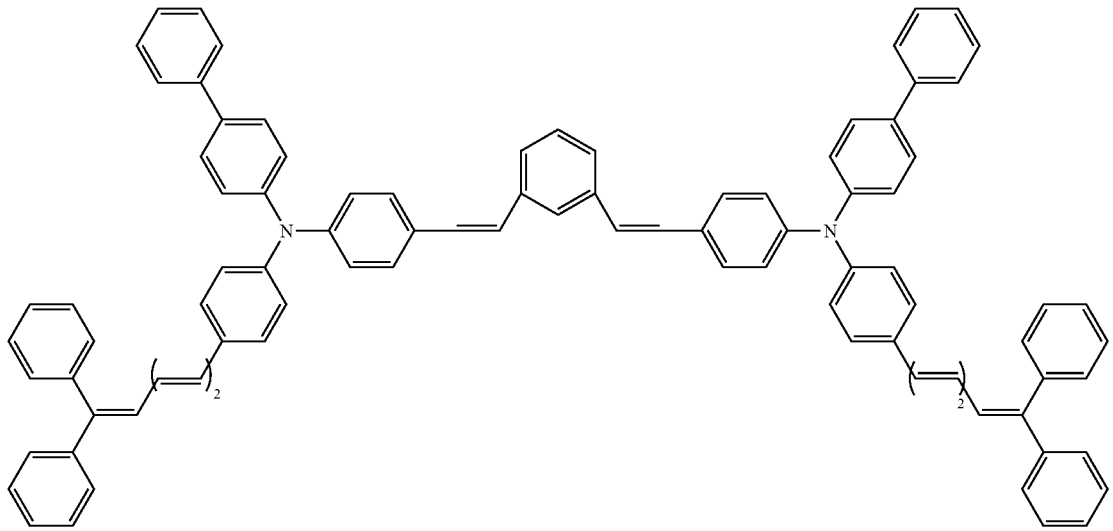
(HTM-AH) (73)
TABLE 2
| | CHARGE GENERATING AGENT | HOLE TRANSPORTING AGENT | CHARGE TRANSPORTING AGENT | $V_o$ (V) | $V_r$ (V) | $E_{1/2}$ (sec.) | CRYSTAL- LIZATION | CHARGING VARIATION (V) |
|---|---|---|---|---|---|---|---|---|
| EXAMPLE 19 | CGM-A | HTM-J | — | 701 | 103 | 0.99 | very good | 24 |
| EXAMPLE 20 | CGM-A | HTM-J | ETM-A | 700 | 93 | 0.87 | very good | 18 |
| EXAMPLE 21 | CGM-A | HTM-J | ETM-B | 700 | 96 | 0.88 | very good | 17 |
| EXAMPLE 22 | CGM-A | HTM-J | ETM-C | 699 | 95 | 0.88 | very good | 17 |

TABLE 2-continued

| | CHARGE GENERATING AGENT | HOLE TRANSPORTING AGENT | CHARGE TRANSPORTING AGENT | $V_o$ (V) | $V_r$ (V) | $E_{1/2}$ (sec.) | CRYSTAL-LIZATION | CHARGING VARIATION (V) |
|---|---|---|---|---|---|---|---|---|
| EXAMPLE 23 | CGM-A | HTM-K | — | 702 | 104 | 0.96 | very good | 22 |
| EXAMPLE 24 | CGM-A | HTM-K | ETM-A | 701 | 95 | 0.85 | very good | 19 |
| EXAMPLE 25 | CGM-A | HTM-K | ETM-B | 701 | 99 | 0.87 | very good | 17 |
| EXAMPLE 26 | CGM-A | HTM-K | ETM-C | 702 | 97 | 0.86 | very good | 15 |
| EXAMPLE 27 | CGM-A | HTM-L | — | 699 | 112 | 0.94 | good | 28 |
| EXAMPLE 28 | CGM-A | HTM-L | ETM-A | 701 | 108 | 0.84 | good | 22 |
| EXAMPLE 29 | CGM-A | HTM-L | ETM-B | 700 | 103 | 0.86 | good | 23 |
| EXAMPLE 30 | CGM-A | HTM-L | ETM-C | 701 | 102 | 0.86 | good | 22 |
| EXAMPLE 31 | CGM-A | HTM-M | ETM-A | 700 | 107 | 0.87 | good | 24 |
| EXAMPLE 32 | CGM-A | HTM-N | ETM-A | 701 | 104 | 0.86 | good | 24 |
| EXAMPLE 33 | CGM-A | HTM-O | ETM-A | 702 | 98 | 0.86 | good | 21 |
| EXAMPLE 34 | CGM-A | HTM-P | ETM-A | 701 | 102 | 0.9 | very good | 17 |
| EXAMPLE 35 | CGM-A | HTM-Q | ETM-A | 700 | 103 | 0.88 | good | 21 |
| EXAMPLE 36 | CGM-A | HTM-R | ETM-A | 701 | 91 | 0.84 | very good | 17 |
| EXAMPLE 37 | CGM-A | HTM-T | ETM-A | 700 | 95 | 0.85 | very good | 18 |
| EXAMPLE 38 | CGM-A | HTM-U | ETM-A | 703 | 94 | 0.86 | very good | 17 |
| COMPARATIVE EXAMPLE 15 | CGM-A | HTM-AE | — | 700 | 212 | 1.54 | bad | 38 |
| COMPARATIVE EXAMPLE 16 | CGM-A | HTM-AE | ETM-A | 701 | 178 | 1.44 | bad | 34 |
| COMPARATIVE EXAMPLE 17 | CGM-A | HTM-AE | ETM-B | 699 | 181 | 1.48 | bad | 33 |
| COMPARATIVE EXAMPLE 18 | CGM-A | HTM-AE | ETM-C | 702 | 182 | 1.49 | bad | 35 |
| COMPARATIVE EXAMPLE 19 | CGM-A | HTM-AF | — | 701 | 232 | 1.67 | bad | 40 |
| COMPARATIVE EXAMPLE 20 | CGM-A | HTM-AF | ETM-A | 702 | 195 | 1.54 | bad | 37 |
| COMPARATIVE EXAMPLE 21 | CGM-A | HTM-AF | ETM-B | 701 | 201 | 1.58 | bad | 33 |
| COMPARATIVE EXAMPLE 22 | CGM-A | HTM-AF | ETM-C | 700 | 200 | 1.57 | bad | 33 |
| COMPARATIVE EXAMPLE 23 | CGM-A | HTM-AG | ETM-A | X | X | X | bad | X |
| COMPARATIVE EXAMPLE 24 | CGM-A | HTM-AH | ETM-A | 699 | 173 | 1.44 | bad | 32 |

*Symbol X in each of the columns of initial charging potential ($V_o$), residual potential ($V_r$), and half decay exposure ($E_{1/2}$) means that no evaluation was conducted because of crystallized photoconductor.

INDUSTRIAL APPLICATIONS

As described above, the stilbene derivative compound represented by the general formula (1) of the present invention has a specific substrate at a specific position to cause specified steric hindrance, so that such a compound can be distinguished with its good compatibility to a binder resin and good uniform dispersibility in photoconductive layer. Therefore, when it is employed as a hole transporting agent or the like of the electrophotographic photoconductor, an electrophotographic photoconductor that hardly causes crystallization and keeps specified photosensitivity for long periods of time can be obtained. In other words, the electrophotographic photoconductor of the present invention is expected to make a contribute to speeding up, advanced performance, and improved durability of various kinds of image-forming apparatuses, such as an electrostatic copying machine and a laser beam printer.

Furthermore, the stilbene derivative compound represented by the general formula (1) is excellent in hole-transporting ability and durability, so that such a compound can be suitably employed as a hole transporting agent in an electrophotographic photoconductor and also employed in various fields including solar cells and electroluminescence devices.

The invention claimed is:

1. A stilbene derivative represented by the general formula (1):

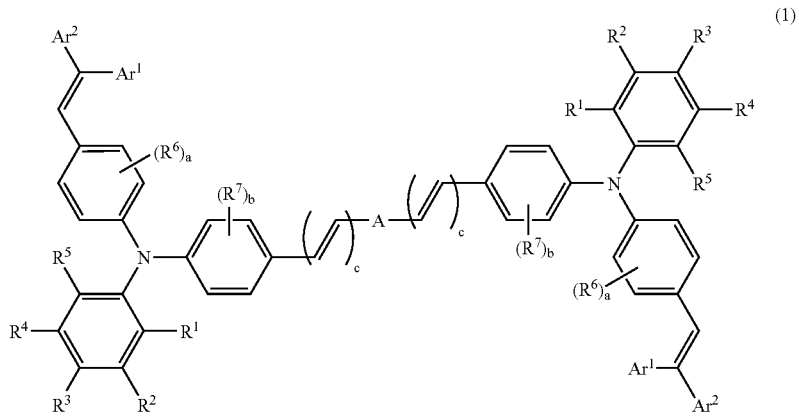

(wherein A is a divalent organic group having an aromatic hydrocarbon as a basic skeleton and is represented by the following formula (2));

plural $R^1$ to $R^7$ are independent substituents, respectively, each of which is a hydrogen atom, a halogen atom, a substituted or unsubstituted alkyl group having 1 to 20 carbon atoms, a substituted or unsubstituted halogenated alkyl group having 1 to 20 carbon atoms, a substituted or unsubstituted alkoxy group having 1 to 20 carbon atoms, a substituted or unsubstituted aryl group having 6 to 30 carbon atoms, or a substituted or unsubstituted amino group, or two of the plural $R^1$ to $R^7$ may be bound or condensed to form a carbon ring structure;

plural $Ar^1$ and $Ar^2$ are independent from each other, each of which is a substituted or unsubstituted aryl group having 6 to 30 carbon atoms;

a and b are numbers of repetition, each of which is an integer from 0 to 4; and c is an integer from 1 to 3, but at least one of the plural $R^1$ and $R^5$ is a substituent other than a hydrogen atom);

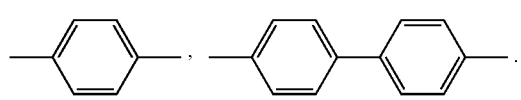

(2)

2. The stilbene derivative compound as described in claim 1, wherein the plural $Ar^1$ and $Ar^2$ in the general formula (1) is a substituted or unsubstituted aryl group having 6 to 14 carbon atoms.

3. The stilbene derivative compound as described in claim 1, wherein the A in the general formula (1) is the divalent organic group represented by the general formula (2), at least one of the plural $R^1$ and $R^5$ is a substituted or unsubstituted alkyl group having 1 to 10 carbon atoms or substituted or unsubstituted alkoxy group having 1 to 10 carbon atoms.

4. The stilbene derivative compound as described in claim 1, wherein two of the plural $R^1$ to $R^5$ in the general formula (1) are bound together to form a carbocyclic ring structure having 3 to 6 carbon atoms.

5. The stilbene derivative compound as described in claim 1, wherein the stilbene derivative compound represented by the general formula (1) is a stilbene derivative compound represented by the following general formula (3):

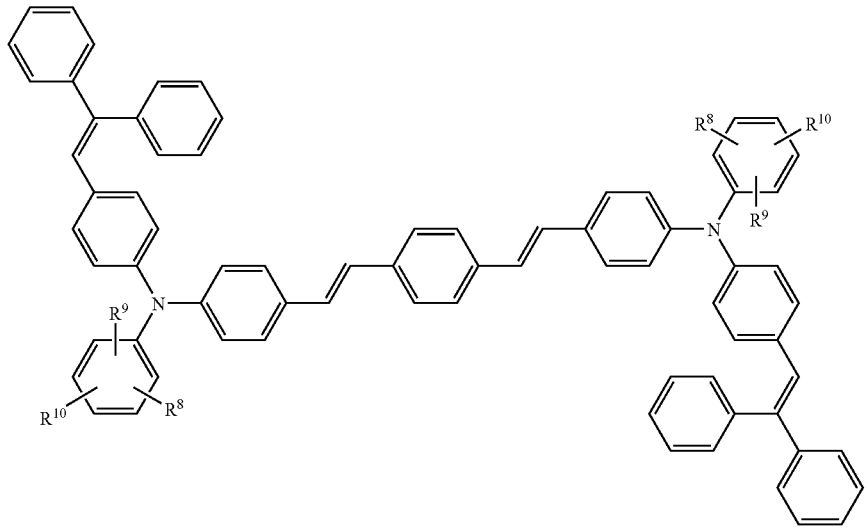

(3)

(wherein plural $R^8$ to $R^{10}$ are independent substituents, respectively, each of which is a hydrogen atom, a halogen atom, a substituted or unsubstituted alkyl group having 1 to 20 carbon atoms, a substituted or unsubstituted halogenated alkoxy group having 1 to 20 carbon atoms, a substituted or unsubstituted aryl group having 6 to 20 carbon atoms, or a substituted or unsubstituted amino group, but at least one of the plural $R^8$, $R^9$ and $R^{10}$ is a substituent positioned at an ortho position of a benzene ring, other than a hydrogen atom.)

6. The stilbene derivative compound as described in claim 5, wherein at least one of the plural $R^8$, $R^9$ and $R^{10}$ in general formula (3) is a substituted or unsubstituted alkyl group having 1 to 6 carbon atoms or substituted or unsubstituted alkoxy group having 1 to 6 carbon atoms, positioned at an ortho position of a benzene ring.

7. An electrophotographic photoconductor comprising a photoconductive layer mounted on an electroconductive substrate, wherein the photoconductive layer contains a stilbene derivative compound represented by the following general formula (1):

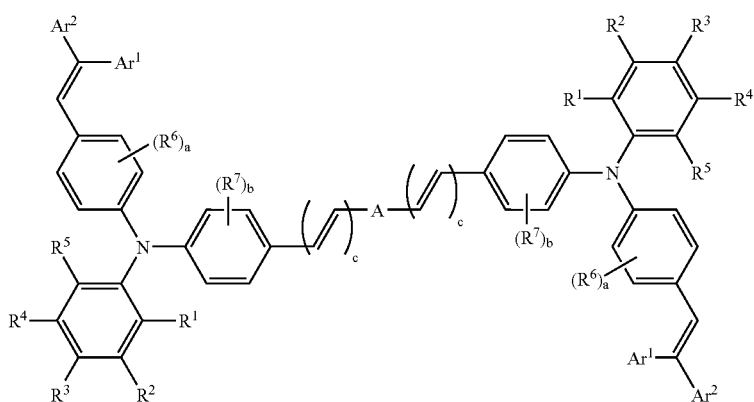

(wherein A is a divalent organic group having an aromatic hydrocarbon as a basic skeleton;

plural $R^1$ to $R^7$ are independent substituents, respectively, each of which is a hydrogen atom, a halogen atom, a substituted or unsubstituted alkyl group having 1 to 20 carbon atoms, a substituted or unsubstituted halogenated alkyl group having 1 to 20 carbon atoms, a substituted or unsubstituted alkoxy group having 1 to 20 carbon atoms, a substituted or unsubstituted aryl group having 6 to 30 carbon atoms, or a substituted or unsubstituted amino group, or two of the plural $R^1$ to $R^7$ may be bound or condensed to form a carbon ring structure; plural $Ar^1$ and $Ar^2$ are independent from each other, each of which is a substituted or unsubstituted aryl group having 6 to 30 carbon atoms; a and b are numbers of repetition, each of which is an integer from 0 to 4; and c is an integer from 1 to 3, but at least one of the plural $R^1$ and $R^5$ is a substituent other than a hydrogen atom when A is a divalent organic group represented by the following formula (2), while at least one of the plural $R^1$ to $R^7$ is a substituent other than a hydrogen atom when A is one other than the divalent organic group represented by the following formula (2));

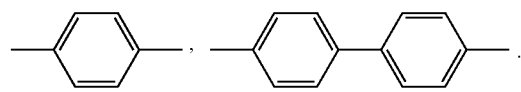

8. The electrophotographic photoconductor as described in claim 7, wherein the stilbene derivative compound represented by the general formula (1) and used in the electrophotographic photoconductor is a stilbene derivative compound represented by the following general formula (3):

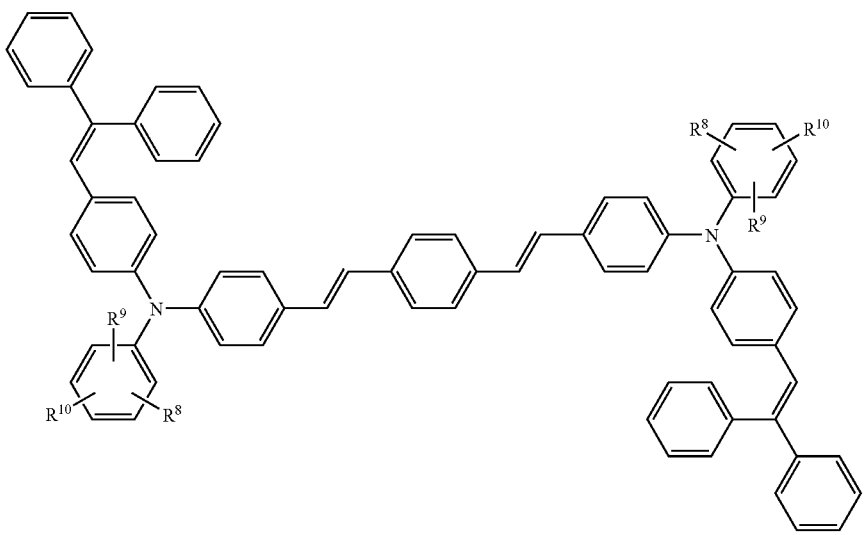

(wherein plural $R^8$ to $R^{10}$ are independent substituents, respectively, each of which is a hydrogen atom, a halogen atom, a substituted or unsubstituted alkyl group having 1 to 20 carbon atoms, a substituted or unsubstituted alkoxy group having 1 to 20 carbon atoms, a substituted or unsubstituted aryl group having 6 to 20 carbon atoms, or a substituted or unsubstituted amino group, but at least one of the plural $R^8$, $R^9$ and $R^{10}$ is a substituent positioned at an ortho position of a benzene ring, other than a hydrogen atom.)

9. The electrophotographic photoconductor as described in claim 7, wherein the photoconductive layer is of a monolayer type, further comprising a charge generating agent and an electron transporting agent.

* * * * *